United States Patent
Lesuisse et al.

(10) Patent No.: US 6,794,415 B2
(45) Date of Patent: Sep. 21, 2004

(54) BIPHENYL COMPOUNDS AND THEIR USE AS OESTROGENIC AGENTS

(75) Inventors: Dominique Lesuisse, Paris (FR); Jean-Georges Teutsch, Pantin (FR)

(73) Assignee: Aventis Pharma S.A. (FR)

(*) Notice: Subject to any disclaimer, the term of this patent is extended or adjusted under 35 U.S.C. 154(b) by 185 days.

(21) Appl. No.: 10/190,497

(22) Filed: Jul. 8, 2002

(65) Prior Publication Data

US 2004/0043993 A1 Mar. 4, 2004

Related U.S. Application Data

(62) Division of application No. 09/896,943, filed on Jun. 29, 2001, now Pat. No. 6,563,008, which is a division of application No. 09/117,628, filed as application No. PCT/FR97/00183 on Jan. 30, 1997, now Pat. No. 6,288,126.

(30) Foreign Application Priority Data

Feb. 1, 1996 (FR) .............................................. 96 01211

(51) Int. Cl.[7] .......................... A61K 31/11; C07C 45/00; C07C 39/00
(52) U.S. Cl. ...................... 514/700; 514/726; 514/731; 514/681; 568/441; 568/716; 568/744
(58) Field of Search .................................. 568/441, 716, 568/734, 744; 514/700, 726, 731, 681

(56) References Cited

U.S. PATENT DOCUMENTS 6,288,126 B1 * 9/2001 Lesuisse et al. ............ 514/681
6,563,008 B2 * 5/2003 Lesuisse et al. ............ 568/716

* cited by examiner

*Primary Examiner*—Johann Richter
*Assistant Examiner*—Sikarl A. Witherspoon
(74) *Attorney, Agent, or Firm*—Muserlian, Lucas and Mercanti

(57) ABSTRACT

A method of treating osteoporosis in warm-blooded animals comprising administering to warm-blooded animals in need thereof an effective amount to treat osteoporosis of a compound selected from the group consisting of a compound of the formula:

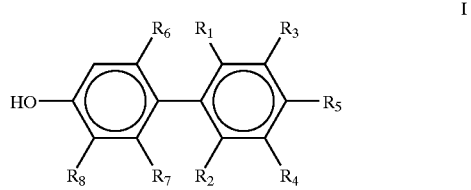

wherein the substituents are defined as in the Specification.

9 Claims, No Drawings

BIPHENYL COMPOUNDS AND THEIR USE AS OESTROGENIC AGENTS

PRIOR APPLICATIONS

This application is a division of U.S. patent application Ser. No. 09/896,943 filed Jun. 29, 2001 now U.S. Pat. No. 6,563,008, which is a division of U.S. patent application Ser. No. 09/117,628 filed Sep. 28, 1998, now U.S. Pat. No. 6,288,126, which is a 371 of PCT/FR97/00183 filed Jan. 30, 1997.

The present invention relates to the use as medicaments of biphenyl compounds, the pharmaceutical compositions containing them, new biphenyl compounds, their preparation process and the intermediates of this process.

A subject of the invention is as medicaments the compounds of general formula (I):

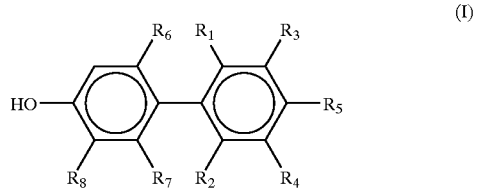

in which $R_1$ and $R_2$, identical or different, represent a hydrogen atom, a halogen atom, a hydroxyl radical, a trifluoromethyl radical, a nitro radical, an amino radical, an alkyloxy, alkylthio, alkylamino or dialkylamino radical, in which the alkyl contains from 1 to 8 carbon atoms, an —$NR_AR_B$ group, in which $R_A$ and $R_B$ form with the nitrogen atom to which they are linked a saturated or unsaturated heterocycle with 5 to 6 members optionally containing another heteroatom chosen from N, O and S, a linear or branched alkyl, alkenyl or alkynyl radical, each containing at most 8 carbon atoms and optionally substituted, an aryl radical containing from 6 to 14 carbon atoms and optionally substituted, an aralkyl radical containing from 7 to 15 carbon atoms and optionally substituted, or a CH(OH)—Y or C(O)—Y radical in which Y represents a substituted or non-substituted alkyl, alkenyl or alkynyl radical containing from 1 to 8 carbon atoms, or a substituted or non-substituted aryl group containing from 6 to 14 carbon atoms, or also $R_1$ can form together with $R_3$ a —CH=CH—CH=CH— group, $R_3$ and $R_4$, identical or different, represent a hydrogen atom, a halogen atom or an alkyl radical containing from 1 to 8 carbon atoms, or $R_3$ can form together with $R_1$ a —CH=CH—CH=CH— group, $R_6$ and $R_7$ identical or different, represent a hydrogen atom or a halogen atom, $R_8$ represents a hydrogen atom or an optionally substituted benzyl radical and $R_5$ represents an [A]—$CH_3$, —[A]—C(OH)ZZ' or —[A]—C(O)Z'' group in which —[A]— represents a linear or branched alkylene, alkenylene or alkynylene radical each containing at most 8 carbon atoms or a single bond, and Z, Z' and Z'' represent a hydrogen atom, an alkyl, alkenyl or alkynyl radical containing up to 8 carbon atoms or an aryl radical containing from 6 to 14 carbon atoms and optionally substituted, as well as their addition salts with pharmaceutically acceptable acids and bases, it being understood that there are excluded the compounds in which $R_5$ represents the [A]—C(O)—Z'' group in which [A] is a single bond, Z'' is an alkyl radical containing from 1 to 8 carbon atoms and $R_1$, $R_2$, $R_3$, $R_4$, $R_6$, $R_7$ and $R_8$ are hydrogen atoms.

By halogen atom is meant fluorine, iodine, bromine and chlorine.

By alkyloxy radical containing from 1 to 8 carbon atoms, is preferably meant the radical chosen from methoxy, ethoxy, propoxy, butoxy and pentoxy.

By alkylthio radical containing from 1 to 8 carbon atoms, is preferably meant the radical chosen from methylthio, ethylthio, propylthio, isopropylthio and butylthio.

By alkylamino radical containing from 1 to 8 carbon atoms is preferably meant the radical chosen from methylamino, ethylamino, propylamino, butylamino, pentylamino.

By dialkylamino radical each containing from 1 to 8 carbon atoms is preferably meant the radical chosen from dimethylamino, diethylamino and methylethylamino.

By —$NR_AR_B$ group is preferably meant the group chosen from pyrrolidinyl, piperidinyl, piperazinyl, morpholinyl, thiamorpholinyl and pyrrolyl.

By linear or branched alkyl, alkenyl or alkynyl radical, each containing at most 8 carbon atoms is preferably meant the radical chosen from methyl, ethyl, propyl, isopropyl, butyl, isobutyl, tert-butyl, n-pentyl, n-hexyl, 2-methyl pentyl, 2,3-dimethyl butyl, n-heptyl, 2-methylhexyl, 2,2-dimethyl pentyl, 3,3-dimethyl pentyl, 3-ethylpentyl, n-octyl, 2,2-dimethylhexyl, 3,3-dimethylhexyl, 3-methyl 3-ethylpentyl, vinyl, propenyl, isopropenyl, allyl, 2-methylallyl, butenyl, isobutenyl, ethynyl, propynyl, propargyl, butynyl and isobutynyl and most particularly the methyl, ethyl, vinyl, propenyl, ethynyl and propynyl radical.

By aryl radical containing from 6 to 14 carbon atoms and aralkyl containing from 7 to 15 carbon atoms and optionally substituted, is preferably meant a phenyl or benzyl radical optionally substituted by a halogen atom chosen from fluorine, chlorine, bromine and iodine, an alkyl radical having from 1 to 8 carbon atoms such as methyl, ethyl, propyl, isopropyl, butyl, isobutyl, tert-butyl, an alkoxy radical having from 1 to 8 carbon atoms such as methoxy, ethoxy, propyloxy, isopropyloxy, butyloxy, an alkylthio radical having from 1 to 8 carbon atoms such as methylthio, ethylthio, propylthio, isopropylthio, butylthio, an amino, alkylamino radical having from 1 to 8 carbon atoms such as methylamino or ethylamino, dialkylamino having 2 to 16 carbon atoms such as dimethylamino, diethylamino, methylethylamino, each of these dialkylamino radicals being optionally in oxidized form, an aminoalkyl radical having from 1 to 8 carbon atoms such as aminomethyl or aminoethyl, a dialkylaminoalkyl radical having from 3 to 16 carbon atoms such as dimethylamino methyl or ethyl, a dialkylaminoalkyloxy radical having from 3 to 16 carbon atoms such as in particular the dimethylamino ethyloxy radical, a hydroxyl group, a free, esterified carboxy group such as alkoxy carbonyl for example methoxy carbonyl or ethoxy carbonyl or salified by a sodium or potassium atom, a cyano radical, a trifluoromethyl radical, a nitro radical, a formyl radical, a carbamoyl radical, an acyl group such as acetyl, propionyl, butyryl or benzoyl, acyloxy having up to 12 carbon atoms such as acetoxy or a group of formula: —O—CO—$(CH_2)_m CO_2H$ in which m is an integer ranging from 1 to 5, an alkenyl radical such as vinyl or propenyl, an alkynyl radical such as ethynyl or propynyl, an aryl radical such as phenyl, furyl, thienyl or aralkyl such as benzyl.

The expression "optionally substituted aryl" indicates that one or more substituents, identical or different, can be present in the ortho, meta or para position.

When $R_1$ and $R_2$ are substituted alkyl, alkenyl or alkynyl radicals, they are the substituents as defined above.

The invention naturally extends to the salts of the compounds of formula (I), such as for example the salts formed when the compounds of formula (I) contain an amino function, with hydrochloric, hydrobromic, nitric, sulphuric, phosphoric, acetic, formic, propionic, benzoic, maleic, fumaric, succinic, tartaric, citric, oxalic, glyoxylic, aspartic, alkanesulphonic acids such as methane or ethanesulphonic acids, arenesulphonic acids, such as benzene or paratoluene sulphonic acids and arylcarboxylic acids, or when the compounds of formula (I) contain an acid function, with the salts of the alkali or alkaline earth metals or ammonium optionally substituted.

A particular subject of the invention as medicaments is the compounds of formula (I) as defined previously corresponding to general formula (I'):

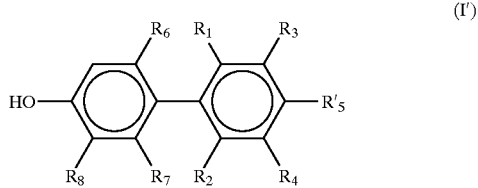

in which
either $R'_5$ represents an —[A]—CHO radical as defined previously and $R_1$, $R_2$, $R_3$, $R_4$, $R_6$, $R_7$ and $R_8$ are as defined previously, it being understood that when [A] represents a single bond and $R_3$, $R_4$, $R_6$, $R_7$ and $R_8$ are hydrogen atoms, $R_1$ and $R_2$ cannot simultaneously represent a hydrogen atom, or $R'_5$ represents an —[A]—C(OH)ZZ' group as defined previously and $R_1$, $R_2$, $R_3$, $R_4$, $R_6$, $R_7$ and $R_8$ are as defined previously, it being understood that when [A] represents a single bond and $R_3$, $R_4$, $R_6$, $R_7$, and $R_8$ are hydrogen atoms, $R_1$ and $R_2$ cannot simultaneously represent a hydrogen atom, or $R'_5$ represents an —[A]—$CH_3$ radical as defined previously and $R_1$, $R_2$, $R_3$, $R_4$, $R_6$, $R_7$ and $R_8$ are as defined previously, it being understood that when $R_3$, $R_4$, $R_6$, $R_7$ and $R_8$ are hydrogen atoms, $R_1$ and $R_2$ cannot simultaneously each represent a hydrogen atom, and it being understood that $R_1$, $R_2$, $R_3$ or $R_4$ cannot represent an alkyl radical or a halogen atom, or $R'_5$ represents an [A]—C(O)Z'' radical as defined previously, $R_1$, $R_2$, $R_3$, $R_4$, $R_6$, $R_7$ and $R_8$ are as defined previously, it being understood that when [A] represents a single bond, $R_3$, $R_4$, $R_6$, $R_7$ and $R_8$ are hydrogen atoms, and Z'' is an alkyl radical containing from 1 to 8 carbon atoms, so $R_1$ and $R_2$ cannot simultaneously each represent a hydrogen atom, or cannot represent a nitro or hydroxyl radical, as well as their addition salts with pharmaceutically acceptable acids and bases.

A more particular subject of the invention as medicaments is the compounds of general formula (I') as defined previously, in which $R_1$, $R_2$, $R_3$, $R_4$, $R_6$, $R_7$ and $R_8$ are as defined previously and in which —[A]— represents a single bond, as well as the addition salts with pharmaceutically acceptable acids or bases.

When $R'_5$ represents an [A]—C(O)Z'' group, [A] is preferably a single bond. This is preferably a radical chosen from formyl, acetyl, propionyl, butyryl and benzoyl.

A quite particular subject of the invention as medicaments is the compounds of formula (I') as defined previously in which $R_1$, $R_2$, $R_3$, $R_4$, $R_6 R_7$ and $R_8$ have the same meaning as previously and in which $R'_5$ represents a formyl radical as well as the addition salts with pharmaceutically acceptable acids or bases.

A quite particular subject of the invention is also as medicaments the compounds of formula (I') as defined previously in which $R_1$, $R_2$, $R_3$, $R_4$, $R_6$, $R_7$ and $R_8$ have the same meaning as previously and in which $R'_5$ represents an —[A]—C(OH)ZZ' group as defined previously, as well as the addition salts with pharmaceutically acceptable acids or bases.

When, $R'_5$ represents an [A]—C(OH)ZZ' radical, [A] is preferably a single bond or an alkylene group of formula —$(CH_2)_n$—, in which n represents an integer comprised between 1 and 8, such as —$CH_2$—, —$CH_2CH_2$—, —$CH_2CH_2CH_2$— or —$CH_2CH_2CH_2CH_2$—, Z and Z' preferably represent a hydrogen atom, an alkyl radical or a phenyl radical.

A most particular subject of the invention as medicaments is the compounds of formula (I') as defined previously in which $R'_5$ represents a $CH_2OH$ radical and $R_1$, $R_2$, $R_3$, $R_4$, $R_6$, $R_7$ and $R_8$ have the same meaning as previously as well as the addition salts with pharmaceutically acceptable acids and bases.

When $R'_5$ represents an [A]—$CH_3$ radical, [A] is preferably a single bond or a $CH_2$, $CH(CH_3)$, $C(CH_3)_2$, $CH_2CH_2$, $CH_2CH_2CH_2$ or $CH_2CH_2CH_2CH_2$ group.

A more particular subject of the invention is as medicaments the compounds of formula (I') as defined previously in which $R_6$, $R_7$ and $R_8$ are hydrogen atoms.

A more particular subject of the invention is as medicaments the compounds of formula (I') as defined previously in which $R_6$ and $R_7$ are hydrogen atoms and $R_8$ is a benzyl group.

A quite particular subject of the invention as medicaments is the compounds of formula (I') as defined previously in which $R_1$ and $R_2$ identical or different are halogen atoms and $R_3$, $R_4$, $R_6$, $R_7$ and $R_8$ are hydrogen atoms.

A quite particular subject of the invention as medicaments is the compounds of formula (I) as defined previously corresponding to general formula (I''):

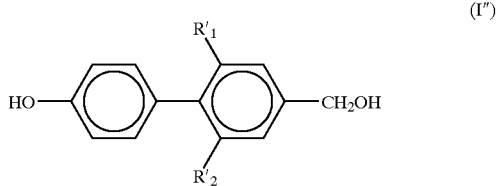

in which $R'_1$ represents an aryl group containing from 6 to 14 carbon atoms and optionally substituted, $R'_2$ represents a halogen atom, a nitro radical or an amino radical, as well as the addition salts with pharmaceutically acceptable acids and bases.

A quite particular subject of the invention as medicaments is the compounds of formula (I) as defined previously corresponding to general formula (I'') as defined above in which $R'_1$ represents a phenyl radical substituted by a dialkylaminoalkyloxy group having 3 to 16 carbon atoms and more particularly the dimethylaminoethyloxy radical, as well as the addition salts with pharmaceutically acceptable acids and bases.

A more specific subject of the invention as medicaments is the compounds of formula (I) as defined previously the names of which follow:

2,6-dibromo-4'-hydroxy-(1,1'-biphenyl)-4-methanol,
2,6-dichloro-4'-hydroxy-(1,1'-biphenyl)-4-methanol,
2,6-dinitro-4'-hydroxy-(1,1'-biphenyl)-4-methanol,
4,4''-dihydroxy-(1,1':2',1''-terphenyl)-5'-methanol,
1-[2-chloro-4'-hydroxy-3-methyl-6-(1-methylethyl))-(1,1'-biphenyl-4-yl)]-ethanone, 2-bromo-4'-hydroxy-6-nitro-(1,1'-biphenyl)-4-methanol, 1-[2-chloro-4'-hydroxy 3-methyl-6-(1-methylethyl)-(1,1'-biphenyl-4-yl)]-ethanol, 4'-hydroxy-2-trifluoromethyl-(1,1'-biphenyl)-4-methanol, 4'-methyl-2'-trifluoromethyl-(1,1'-biphenyl)-ol, 2,6-dichloro-4'-hydroxy-(1,1'-biphenyl)-4-carboxaldehyde, 2-chloro-4'-hydroxy-6-(1-methylethyl)-(1,1'-biphenyl)-4-methanol, 2-chloro-4'-hydroxy-6-trifluoromethyl-(1,1'-biphenyl)-4-methanol, 2,6-dichloro-4'-hydroxy-5'-(phenylmethyl)-(1,1'-biphenyl)-4-methanol, 2-bromo 6-[[4-[2-(dimethylamino) ethoxy] phenyl] hydroxymethyl] 4'-hydroxy (1,1'-biphenyl) 4-methanol,

[6-bromo 4'-hydroxy 4-(hydroxymethyl) (1,1'-biphenyl) 2-yl] [4-[2-(dimethylamino) ethoxy] phenyl] methanone, 6'-bromo 4-[2-(dimethylamino) ethoxy] 4"-hydroxy (1,1':2',1"-terphenyl) 4'-methanol, 4-[2-(dimethylamino) ethoxy] 4"-hydroxy 6'-nitro (1,1':2',1"-terphenyl) 4'-methanol, 6'-chloro 4,4"-dihydroxy (1,1':2',1"-terphenyl) 4'-methanol.

The Applicant has demonstrated that the compounds of formula (I) as well as their addition salts with pharmaceutically acceptable acids and bases are particularly useful products from a pharmacological point of view. They are original ligands of the oestrogen receptor.

As such, the products of formula (I) can be used in the treatment of disorders linked to hypofolliculinemia, for example, amenorrheas, dysmenorrheas, repeated abortions, premenstrual disorders, in the treatment of certain oestrogen-dependent pathologies such as prostatic adenomas or carcinomas, mammary carcinomas and their metastases or in the treatment of benign tumours of the breast, both as an antiuterotropic as well as in the replacement treatment of symptoms linked to the menopause and in particular of osteoporosis.

The invention extends to the pharmaceutical compositions containing at least one medicament as defined above as active ingredient.

The compounds of formula (I) are used by digestive, parenteral or local route, for example by percutaneous route. They can be prescribed in the form of simple or sugar-coated tablets, capsules, granules, suppositories, pessaries, injectable preparations, ointments, creams, gels, microspheres, implants, patches, which are prepared according to the usual methods.

The active ingredient or ingredients can be incorporated with excipients usually used in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersion or emulsifying agents, preservatives.

The dose varies according to the illness to be treated and the administration route: it can vary for example from 1 mg to 100 mg by day in adults by oral route.

Certain products of formula (I) are new and are therefore a subject of the present invention.

Others are known.

Certain products of general formula (I) with $R_5$ representing an [A]—C(OH)ZZ' group and $R_1$, $R_2$, $R_3$, $R_4$, $R_6$, $R_7$ and $R_8$ are hydrogens, are known as intermediate synthetic products or also in the field of liquid crystals. There can be mentioned the following examples:

| | |
|---|---|
| $R_5$ = CH(CH$_3$)OH | US 5218124 (1993) |
| $R_5$ = CMe$_2$OH | DE 3402831 (1984) |

Certain products of general formula (I) with $R_5$ representing an [A]—CH$_3$ group are used in the field of liquid crystals. There can be mentioned the following examples:

$R_1$=Cl and $R_5$=n-Pentyl, Liq. Cryst. 10(6), 799–802

$R_1$=Me and $R_5$=n-Pentyl, Liq. Cryst. 10(6), 799–802

$R_1$=F, $R_2$=F and $R_5$=n-Pentyl, GB2257701 (Feb. 1, 1993)

$R_3$=Cl and $R_5$=n-pentyl, CA116-107805.

Certain products of general formula (I) with $R_5$ representing an [A]—COZ" group containing from 2 to 8 carbon atoms are for their part used as synthetic intermediate products (CA 120 77179u $R_5$=acetyl and $R_1$=NO$_2$) or also in the field of liquid crystals (CA 111 245029e $R_5$=C(O)C$_5$ and $R_1$=OH).

Certain products of general formula (I) with $R_5$ representing an [A]—CHO group and $R_1$, $R_2$, $R_3$, $R_4$, $R_5$, $R_6$, $R_7$ and $R_8$ are hydrogens are known as synthetic intermediate products or also in the field of liquid crystals. There can be mentioned the following example:

$R_5$=CHO JP01207254 (1989).

Certain products of general formula (I) with $R_5$ representing an [A]—COOH group are known. There can be mentioned the following example:

$R_5$=—(CH$_2$)$_n$—COOH, n=0, 1 or 2 and $R_1$=R$_2$=I or Cl: A. Dibbo et al. J. Chem. Soc. (1961) 2890–2902.

Thus a subject of the invention is also the use, as a medicament, on the one hand of known products of general formula (I) and on the other hand of new products of general formula (I).

Therefore a subject of the invention is also new compounds of general formula (I) corresponding to formula (I') as described previously, as well as their addition salts with acids and bases.

A quite particular subject of the invention is the compounds of general formula (I) as defined previously listed above.

Another particular subject of the invention is new compounds of formula (I) as defined previously corresponding to general formula (I") as defined above as well as their addition salts with acids and bases.

A subject of the invention is also a preparation process for products of formula (I') as defined above characterized in that a product of formula (II):

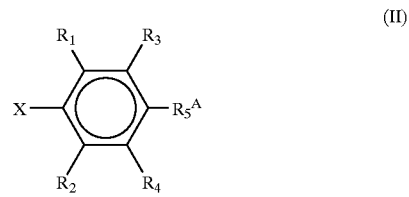

(II)

in which $R_1$, $R_2$, $R_3$ and $R_4$ are as defined previously and $R_{5A}$ has the values of R'$_5$ as defined previously as well as the hydrogen or esterified or non esterified —[A]—CO$_2$H values and X represents a hydrogen atom, halogen or an $OSO_2CF_3$ group, is subjected to the action, in the presence of a catalyst, of a product of formula (III):

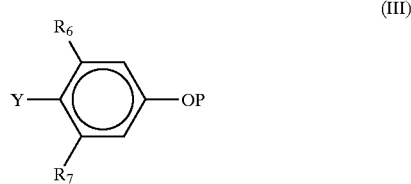

(III)

in which $R_6$ and $R_7$ are as defined previously, Y represents a hydrogen atom, halogen, a $B(OH)_2$ group or an $Sn(R)_3$ group, in which R represents an alkyl group containing from 1 to 8 carbon atoms, and P represents a protective group, in order to obtain a product of formula (IV):

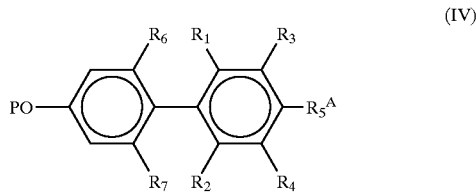

(IV)

in which P, $R_1$, $R_2$, $R_3$, $R_4$, $R_{5A}$, $R_6$ and $R_7$ have the same meaning as previously, which product of formula (IV) if desired or if necessary is subjected in an appropriate order to one or, if appropriate, several of the following reactions in order to obtain the product of formula (I'):

deprotection of the phenol, debenzylation then rearrangement in order to obtain a product of formula (I) with $R_8$=benzyl, total or partial reduction of the $NO_2$ groups which can be represented by $R_1$ or $R_2$ into $NH_2$, substitution of $NH_2$ which can be represented by $R_1$, $R_2$, $R_3$ or $R_4$, by Br or by I, formylation reaction when $R_{5A}$ represents a hydrogen atom, reduction of the esterified —[A]—$CO_2H$ function which can be represented by $R_{5A}$, saponification, reduction of the —[A]—CHO group which can be represented by $R_{5A}$ into an —[A]—$CH_2OH$ group, oxidation of the —[A]—CHO group which can be represented by $R_{5A}$ into an —[A]—$CO_2H$ group, esterification of the —[A]—$CO_2H$ group which can be represented by $R_{5A}$, reduction of the acyl function which can be represented by $R_{5A}$ into the corresponding alcohol, or into the corresponding alkyl radical, Wittig's reaction on the [A]—CHO function which can be represented by $R_5A$ in order to obtain an [A]—CH=CH—CHO group, then reduction of the unsaturated aldehyde in order to obtain the corresponding alcohol of formula [A]—CH=CH—$CH_2OH$, Wittig's reaction on the [A]—CHO function which can be represented by $R_{5A}$ in order to obtain an [A]—$CH_2$—CHO group, then reduction of the [A]—$CH_2$—CHO aldehyde in order to obtain the corresponding alcohol of formula [A]—$CH_2$—$CH_2OH$, reduction reaction when [A] represents a bivalent alkenylene or alkynylene radical, action of an organometallic on the aldehyde, the ketone or the esterified acid which can be represented by $R_{5A}$, formation of a pyrrole group from $NH_2$, substitution of $NH_2$ by an S-Alkyl group, and salification by an acid or a base.

Formation of the biphenyls of formula (IV) by coupling of the aromatic compound of formula (II) with the aromatic compound of formula (III) is carried out either in the presence of a catalyst chosen from palladium derivatives in the case where:

(a) Y represents a $B(OH)_2$ or $Sn(R)_3$ group and X represents an $OSO_2CF_3$ group, a bromine atom or an iodine atom, and thus can be carried out under the conditions described in the following articles when Y represents a $B(OH)_2$ group:

A. Huth, I. Beetz and I. Schumann Tetrahedron (1989) 45 6679: Conditions: $Na_2CO_3$ 2M/Pd(PΦ$_3$)$_4$/Toluene/LiCl/EtOH/Δ

J. K. Stille et al. Ang. Chem. Int. Ed. (1986) 25 508: Conditions: Pd(PΦ$_3$)$_4$/LiCl/Dioxane/Δ

T. Oh-e, N. Migawa and A. Suzuki J. Org. Chem. (1993) 58 2201–2208: Conditions: $K_3PO_4$/KBr/Pd(PΦ$_3$)$_4$/Dioxane/Δ

Suzuki et al., Synlett (1992) 208
Conditions: Pd(PΦ$_3$)$_4$/Ba(OH)$_2$/DMEaq;

or also when Y represents an $SnBu_3$ group, under the conditions described in the following articles:

J. K. Stille et al, J. Am. Chem. Soc. (1987) 5478–5480 or by V. Farina, J. Org. Chem. (1993) 58 5434;

or in the presence of copper in the case where:

(b) Y represents an iodine atom and X represents a chlorine atom, (c) Y represents a chlorine atom and X represents an iodine atom, and thus can be carried out under the conditions described in the following:

P. E. Fanta Chem. Rev. (1964) 38 139 or synthesis (1974) 9: Conditions: Cu/DMF/120° C.;

or in the presence of a strong base and of $ZnCl_2$ then a catalyst chosen from palladium derivatives in the case where:

(d) Y represents a bromine atom and X represents a hydrogen atom, (e) Y represents a hydrogen atom and X represents a bromine atom, and thus can be carried out under the following conditions:

1) nBuli/THF/−768° C.

2) $ZnCl_2$

3) ArBr/Pd(PΦ$_3$)$_4$/Δ

4) HCl/MeOH.

The orthometalation reactions are described for example in the following documents:

T. KRESS Synthesis (1983) 803,

N. IWAO J. Org. Chem. (1990) 55 3623.

Moreover, the exchange reaction with $ZnCl_2$ followed by a coupling reaction has been described by E. Negishi in J. Org. Chem. (1977) 42 182.

The protective group P preferably represents an alkyl radical containing from 1 to 4 carbon atoms, a benzyl group, an $R_CR_DR_ESi$ group, in which $R_C$, $R_D$ and $R_E$ identical or different, independently of one another each represent an alkyl radical containing from 1 to 4 carbon atoms or a phenyl group. This is most particularly the $Si(Me)_2C(Me)_3$ or —$Si(Ph)_2C(Me)_3$ groups.

Deprotection reactions are the standard deprotection methods known to a person skilled in the art. A fairly complete review is provided in the following work: Protective groups in organic synthesis, T. W Greene, John Wiley & sons (1981).

As an example the deprotection reactions when P is a methyl radical can be carried out by the action of tribromoborane in dichloromethane or hydrochloric acid in pyridine, the deprotection reactions when P is a benzyl group can be carried out by the action of hydrogen in the presence of palladium on carbon in ethyl acetate, by the action of trifluoroacetic acid or by the action of trimethylsilyl iodide. The deprotection reactions when P is a tertbutyldiphenylsilyl group can be carried out by the action of tetrabutyl ammonium fluoride (TBAF) in solution in tetrahydrofuran.

At the time of the debenzylation reaction by the action of trifluoroacetic acid, a rearrangement and formation of a deprotected derivative with $R_8$=benzyl can be obtained.

The reduction reaction of the $NO_2$ radical which can be represented by $R_1$ or $R_2$ into an $NH_2$ radical can be carried out by the action of tin dichloride in ethanol under reflux and the monoreduction reaction is preferably carried out by the action of cyclohexene in the presence of palladium dihydroxide in ethanol or tetrahydrofuran under reflux.

The substitution reaction of $NH_2$ which can be represented by $R_1$ or $R_2$ by Br is preferably carried out by the action of hydrobromic acid in the presence of sodium nitrite and of copper bromide in water at 0° C. or by the action of tribromomethane in the presence of terbutylnitrite.

The substitution reaction of $NH_2$ by iodine is preferably carried out by the action of potassium iodide in the presence of sodium nitrite and sulphuric acid or by the action of iodine in the presence of terbutylnitrite.

The formylation reaction when $R_{5A}$ is a hydrogen atom can be carried out in the presence of dimethylformamide and a strong base such as n-butyllithium then hydrolysis with a mineral acid such as hydrochloric acid.

The reduction reaction of the esterified —[A]—$CO_2$H function which can be represented by $R_{5A}$ in order to obtain the corresponding alcohol is carried out for example by the action of lithium aluminium hydride in tetrahydrofuran.

There is particularly meant by esterified —[A]—$CO_2$H, the —$CO_2$Me and —$CO_2$Et groups.

The saponification reaction of the ester function which can be represented by $R_{5A}$ into the corresponding acid is carried out for example by the action of an alkaline base such as soda or potash in tetrahydrofuran or a lower alcohol such as methanol or ethanol.

The reduction reaction of the [A]—CHO group which can be represented by RSA into an [A]—$CH_2$OH group is carried out for example by the action of sodium borohydride in methanol at 0° C. or by the action of hydrogen in the presence of palladium on carbon in ethyl acetate.

The oxidation reaction of the [A]—CHO group which can be represented by $R_{5A}$ into an [A]—$CO_2$H group can be carried out by the action of Jones reagent (chromic acid/sulphuric acid) in a neutral solvant such as acetone, by the action of silver oxide in tetrahydrofuran and 2N soda or by the action of sodium hypochlorite in the presence of aminosulphonic acid.

The esterification reaction of the —[A]—$CO_2$H group which can be represented by $R_{5A}$, can be carried out by the action of ethanol or methanol in the presence of a strong acid such as hydrochloric or sulphuric acid.

The reduction reaction of the [A]—C(O)—Z" group which can be represented by $R_{5A}$ into the corresponding alcohol can be carried out for example by the action of sodium borohydride in methanol.

The reduction reaction of the [A]—C(O)—Z" group which can be represented by $R_{5A}$ into the corresponding alkyl can be carried out by the action of hydrogen in the presence of palladium on carbon in ethyl acetate.

Wittig's reaction on the [A]—CHO function which can be represented by $R_{5A}$ in order to obtain an [A]—CH=CH—CHO group, is carried out by the action of phosphine $\Phi_3$P=CH—CHO.

The reduction of the unsaturated aldehyde [A]—CH=CH—CHO in order to obtain the corresponding alcohol of formula [A]—CH=CH—$CH_2$OH can be carried out by the action of the sodium borohydride in the presence of $CeCl_3$, $7H_2O$ in methanol.

Wittig's reaction on the [A]—CHO function which can be represented by $R_{5A}$ in order to obtain an [A]—$CH_2$—CHO group (homologation reaction) is carried out by the action of phosphine $\Phi_3$P—$CH_2$OMe or $\Phi_2$P(O)—$CH_2$OMe.

The reduction of the aldehyde [A]—$CH_2$—CHO in order to obtain the corresponding alcohol of formula [A]—$CH_2$—$CH_2$OH can be carried out by the methods described above.

The total or partial reduction reaction when [A] represents a bivalent alkenylene or alkynylene radical can be carried out either totally by the action of hydrogen in the presence of a catalyst such as palladium on carbon or a rhodium catalyst such as Wilkinson's reagent or partially (alkynylene becomes alkenylene) by the action of a poisoned catalyst such as palladium on barium sulphate.

The action of an organometallic on the aldehyde, the ketone or the esterified acid which can be represented by $R_{5A}$ provides access to the products of formula (I') in which $R'_5$ represents —[A]—C(OH)ZZ', Z and Z' represents an optionally substituted alkyl, alkenyl, alkynyl or aryl radical.

The organometallic derivative of a phenyl, alkyl, alkenyl or alkynyl radical is chosen from the magnesium compounds of formula AlkMgHal or ArMgHal and the lithium compounds of formula AlkLi or PhLi in which Alk represents an alkyl, alkenyl or alkynyl group containing at most 8 carbon atoms. Ar represents an optionally substituted phenyl and Hal represents a halogen atom. In a preferred implementation of the process, Hal represents a chlorine, bromine or iodine atom, preferably bromine. The reaction medium can then be subjected to a strong acid such as hydrochloric acid or sulphuric acid.

For example the action of Z—MgBr on the compounds of formula (I') in which $R'_5$=CHO provides access to the compounds of formula (I') in which $R'_5$=—CH(Z)—OH.

For example the action of PhMgBr on the compounds of formula (I') in which $R'_5$=CHO provides access to the compounds of formula (I') in which $R'_5$=—CH(Ph)—OH.

For example, the action of Z—MgBr on the compounds of formula (I') in which $R'_5$=COCH$_2$CH$_3$ provides access to the compounds of formula (I') in which $R'_5$=—C(OH)(Z)(Et).

For example, the action of PhMgBr on the compounds of formula (I') in which $R'_5$=COCH$_2$CH$_3$ provides access to the compounds of formula (I') in which $R'_5$=—C(Ph)(Et)—OH.

For example, the action of MeMgBr on the compounds of formula (IV) in which $R_{5A}$=$CO_2$Me provides access to the compounds of formula (IV) in which $R_{5A}$=—C(Me)$_2$—OH.

The formation of an unsaturated heterocycle such as pyrrole from the corresponding amine is carried out by the action of 2,5 dimethoxytetrahydrofuran in the presence of acetic acid.

The substitution reaction of an amine by S-Alkyl is carried out by the action of (Alkyl-S)$_2$ in the presence of tBuNO$_2$.

Salification can be carried out under the usual conditions. The operation is carried out for example in the presence of ethanolic soda. A sodium salt can also be used such as the carbonate or the carbonate acid of sodium or of potassium.

Similarly, salification by an acid is carried out under the usual conditions. The operation is carried out for example with hydrochloric acid, for example in an ethereal solution.

A particular subject of the invention is a preparation process for products of formula (I") as defined above characterized in that a compound of formula (VII):

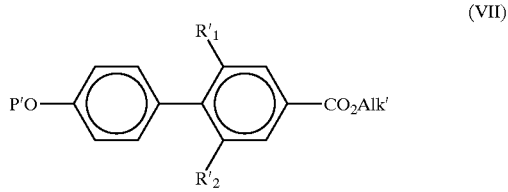

(VII)

in which Alk' and P' identical or different, each represent an alkyl radical containing from 1 to 4 carbon atoms and $R'_1$ and $R'_2$ are as defined previously, is subjected to the action of a deprotection or reducing reagent of the ester function in order to obtain the product of formula (I") then, if desired, is subjected to the action of a base or an acid in order to obtain the corresponding salts.

This product of formula (VII) corresponds to products of formula (IV) in which P represents an alkyl radical containing from 1 to 4 carbon atoms, $R_2$, $R_3$, $R_4$, $R_6$, $R_7$ and $R_8$ are hydrogen atoms, $R_1$ represents an optionally substituted aryl radical and $R_{5A}$ represents an esterified —$CO_2H$ group.

A process for the formation of products of formula (VII), with $R'_1$ representing a Ph—OH group, P and Alk representing a methyl, is described in the following reference:

J. Med. Chem. (1989) 32 1814–1820.

By analogy, this process can thus be extended to all the products of formula (V) with $R'_1$ representing an optionally substituted aryl group containing from 6 to 14 carbon atoms.

Thus a compound of formula (V):

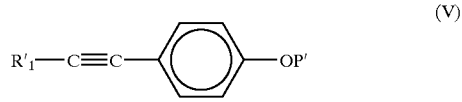

(V)

in which $R'_1$ represents an optionally substituted aryl group and P' represents an alkyl radical containing from 1 to 4 carbon atoms, is subjected to the action of a compound of formula (VI):

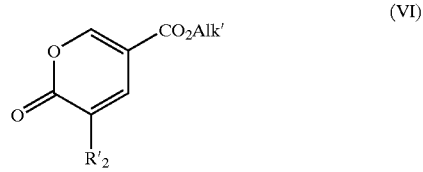

(VI)

in which Alk' represents an alkyl radical containing from 1 to 4 carbon atoms and $R'_2$ is as defined previously, in order to obtain a compound of formula (VII).

The action of the alkylcoumarate of formula (VI) on the compound of formula (V) in order to obtain the compound of formula (VII) is preferably carried out under nitrogen pressure at a temperature of 250° C. in toluene. This reaction is described in the following reference: J. Med. Chem. (1989) 32 1814–1820.

The products of formula (V) are known or are easily accessible to a person skilled in the art by applying the general principles of functionalization of aromatic compounds. There can be mentioned as examples a few references:

WO09309079 ($R'_1$=Ph and P'=Me), J. Organomet. Chem. 395(2), 277–9 ($R'_1$=Ph—$OCH_2CH_2NMe_2$ and P'=Me,).

The products of formula (VI) with $R'_2$=H, are also known. There can be mentioned the following reference: J. Med. Chem. (1989) 32 1814–1820.

The products of formula (VI) with $R'_2$ different from H, are known or easily accessible to a person skilled in the art. For example, the products of formula (VI) with $R'_2$=Cl are formed by action of N-chlorosuccinimide on the product of formula (VI) with $R'_2$=H.

The products of general formula (II) are en general connus or are accessibles to a person skilled in the art by applying the general principles of functionalization of aromatic compounds.

The products of formula (II) with X=OTf (triflates) are obtained from the corresponding alcohols of general formula (II'):

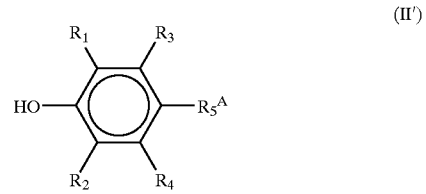

(II')

by the action of triflic anhydride action in pyridine at 0° C. according to the method described by Scott W. J., Stille J. K., J. Am. Chem. Soc. (1986) 108 3033.

The products of general formula (II') are for their part generally known to or are accessible by a person skilled in the art by applying the general principles of the chemistry of aromatic compounds. There can be mentioned among others the following reference: RODD'S CHEMISTRY OF CARBON COMPOUNDS Vol III Aromatic compounds Ed. M. F. ANSELL Elsevier Scientific Publishing Company (1981).

The products of formula (II) with X=I (iodated products) can be obtained by orthometallation from the corresponding non-iodated aromatic products of general formula (II"):

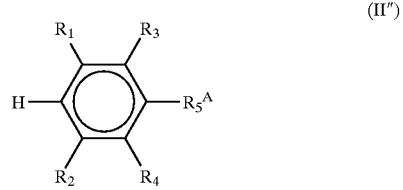

(II")

in particular by the action of N-iodosuccinimide or iodine in the presence of a strong base such as n-Butyllithium in tetrahydrofuran at −78° C.

The products of general formula (II") are for their part generally known to or are accessible by a person skilled in the art by applying the general principles of the chemistry of aromatic compounds.

In the case where $R_{5A}$ is an —[A]—$CO_2H$, [A]—C(O)Z" or —[A]—C(OH)ZZ' group it will be necessary to provide the adequate protections known to a person skilled in the art in particular during the preparation of the products of general formula (II) from products of general formulae (II')

and (II"). As an example, the —[A]—CO$_2$H group can be esterified, the formyl or acyl group can be protected in the form of an acetal such as dioxolane by the action of glycol in the presence of paratoluene sulphonic acid, the hydroxyl group can be protected in the form of a tetrahydropyrranyloxy group (OTHP) by the action of dihydropyrrane.

The products of formula (III) are known or accessible from protected parabromophenol or from parabromoanisole by the following methods: The products of formula (III) with Y representing the B(OH)$_2$ group and P representing a methyl radical can first be obtained by the action of parabromoanisole with Mg turnings in anhydrous diethyl ether under reflux, then by the action of triethylborate in anhydrous diethyl ether at −70° C., then hydrolysis with a strong mineral acid such as sulphuric acid.

The products of formula (III) with Y representing the B(OH)$_2$ group can also be obtained by the action of parabromophenol protected by a protective group P such as benzyl or terbutyldiphenyl silyl, with triethylborate in the presence of n-butyllithium in tetrahydrofuran at −78° C. followed by hydrolysis with a strong mineral acid such as sulphuric acid or with water.

The products of formula (III) with Y representing the SnBu$_3$ group can be obtained by the action of parabromophenol protected by a protective group P such as tertbutyldiphenylsilyl, with tin tributyl chloride in the presence of n-butyllithium in tetrahydrofuran at −78° C.

The products of formula (III) with Y representing an iodine atom and P representing a benzyl or terbutyldiphenylsilyl group can be obtained by the action of paraiodophenol with a protective group as defined above.

A subject of the invention is also as new industrial products and in particular new intermediates necessary for the implementation of the invention, the products of general formula (IV) with the exception of the product of formula (IV) in which R$_{5A}$ represents an esterified or non esterified [A]—CO$_2$H radical.

The following examples illustrate the invention without however limiting it.

Preparation 1

(4-methoxyphenyl)-boronic acid 100 ml of a solution of 10 g of p-bromoanisole in anhydrous diethyl ether is added dropwise under reflux to a suspension, under inert gas, of 1.3 g of magnesium turnings in 5 ml of anhydrous diethyl ether, and the mixture is left under reflux for 2 hours. The reaction medium is then poured into a solution of 9.02 ml of triethylborate in 60 ml of anhydrous ether cooled down to −70° C. After agitation for 1 hour at −70° C., then for 1 hour at ambient temperature, the solution is poured into a mixture comprising 11 ml of sulphuric acid and 50 g of ice and water followed by agitation for 1 hour. The organic phase is extracted with 100 ml of an aqueous solution saturated in sodium bicarbonate, the aqueous phases are combined, then reacidified with 6N hydrochloric acid, extracted with ether, dried and evaporated under reduced pressure. 3.9 g of expected product is obtained.

I.R. spectrum: (Nujol)
Complex absorption OH/NH region, 1609, 1573 and 1518 cm$^{-1}$ NMR (DMSO-d6, 300 MHz)

| | |
|---|---|
| 3.76 s | OC$\underline{H}_3$ |
| 6.88 d J = 9 Hz | H$_3$ and H$_5$ |

-continued

| | |
|---|---|
| 7.78 d J = 9 Hz | H$_2$ and H$_6$ |
| 7.86 | B(OH)$_2$ |

Preparation 2

[4-(phenylmethoxy)phenyl]-boronic acid

Stage A: 1-bromo-4-(phenylmethoxy)-benzene 15.26 g of 50% sodium hydride in oil is added, at 0° C., to a solution under inert gas of 50 g of parabromophenol in 320 ml of dimethylformamide, followed by agitation for 30 minutes at 0° C., then 37.7 ml of benzyl bromide is added. Agitation is carried out for 2 hours 30 minutes while allowing the temperature to return to 20° C., then the reaction mixture is poured into ice-cooled water, the precipitate is filtered and dried. 73.35 g of expected product is obtained.

Rf: 0.85 (thin layer chromatography, support: silica, eluant: cyclohexane/ethyl acetate 7/3).

I.R. spectrum: (CHCl$_3$)

Absence of OH

Aromatic 1592, 1580 and 1488 cm$^{-1}$

Stage B: [4-(phenylmethoxy)phenyl]-boronic acid 143 ml of a solution of n-Butyllithium is added, dropwise, under inert gas and at −78° C., to 47.08 g of the product obtained in Stage A in 375 ml of tetrahydrofuran, agitation is carried out for 1 hour, then 36.5 ml of triethylborate is added. Agitation is carried out for 14 hours, while allowing the temperature to return to 20° C., and the reaction medium is hydrolyzed using a solution of ice-cooled water containing 45 ml of concentrated sulphuric acid, for 1 hour at 20° C. The aqueous phase is extracted with ethyl acetate, the organic phases are washed with 2N soda and the aqueous phase is acidified to pH=1 using a solution of 1N hydrochloric acid in order to precipitate the boronic acid. After filtration and drying the precipitate 28.54 g of expected product is obtained.

Rf: 0.16 cyclohexane/ethyl acetate 7/3)

I.R. spectrum: (Nujol)

| | |
|---|---|
| General absorption OH/NH region | 3650, 3615, 3510 and 3420 cm$^{-1}$ |
| Aromatic | 1605, 1570 and 1510 cm$^{-1}$ |
| B—O | 1410, 1340 cm$^{-1}$ |

Preparation 3

[4-[[(1,1-dimethylethyl)diphenylsilyl]oxy]phenyl]-boronic acid

Stage A: 1-Bromo-4-[[(1,1-dimethylethyl)diphenylsilyl]oxy]benzene 400 ml of dimethylformamide, 31.18 g of imidazole and 125.89 g of 1,1-dimethyl-ethyldiphenyl-chlorosilane are added under an inert atmosphere and at ambient temperature to 80.89 g of parabromophenol, then the solution obtained is agitated for 2 hours. The reaction medium is poured into 2 litres of water, precipitation is observed, the solid is solubilized with ethyl acetate and the aqueous phase is extracted with ethyl acetate, the combined organic phases are dried and evaporated under reduced pressure until an oil is obtained. Pentane is added and crystallisation is observed.

After filtration and drying of the precipitate 179.24 g of expected product is obtained. Rf: 0.53 (thin layer chromatography, support: silica, eluant Cyclohexane/AcOEt 95/5).

Melting point: 56° C.
NMR (CDCl$_3$, 300 MHz)

| | |
|---|---|
| 1.09 s | Si—tBu |
| 6.63 m | H$_3$, H$_5$ |
| 7.17 m | H$_2$, H$_6$ |
| 7.69 dd | 4 H for SiΦ2 |
| 7.4 | 6 H for SiΦ2 |

Stage B: [4-[[(1,1-dimethylethyl)diphenylsilyl]oxy]phenyl]-boronic acid 60 ml of a solution of n-butyl-lithium is added, dropwise, at −78° C. and under inert gas, to a solution of 30 g of the product of the previous stage in 100 ml of anhydrous tetrahydrofuran, followed, after agitation for 30 minutes at −78° C., by the addition of 9.95 ml of trimethylborate. After agitation for 2 hours 30 minutes, while allowing the reaction medium to return to ambient temperature, 20 ml of water is added dropwise and agitation is carried out for 72 hours. After evaporation of the tetrahydrofuran under reduced pressure, the aqueous phase is extracted with ether, dried and concentrated under reduced pressure until an oil is obtained (26.35 g) which is purified by filtration chromatography on silica with a hexane/ethyl acetate mixture 1/1 in order to obtain 7.73 g of expected product in the form of the trimer and the monomer.

| | |
|---|---|
| IR (CHCl$_3$) | |
| O—Si | 915 and 1255 cm$^{-1}$ |
| B—O | 1350 and 1370 cm$^{-1}$ |
| Aromatics | 1515, 1570 and 1602 cm$^{-1}$ |
| NMR (CDCl$_3$) | |
| 1.11 | tBu |
| 6.81 and 7.88 | Ph—O |
| 7.3 to 7.5 (6 H) and 7.72 (4 H) | PhSi |

Preparation 4

[4-[[(1.1-dimethylethyl)diphenylsilyl]oxy]phenyl]-tributyl tin 123.89 ml of a solution of sec-butyl-lithium (1.13 M) is added, dropwise, at −50° C. and under inert gas, to a solution of 50 g of the product of Stage A of Preparation 3 in 300 ml of anhydrous tetrahydrofuran, then after agitation for 1 hour at −50° C., 36.29 ml of tributyl tin chloride is added. After agitation for 30 minutes, while allowing the reaction medium to return to ambient temperature, the reaction mixture is poured into ice-cooled water, the aqueous phase is extracted with ethyl acetate, dried and evaporated to dryness under reduced pressure. 38.5 g of the product is obtained in the form of an oil (T$_{bp}$: 230° C. under 10$^{-2}$ mbar)

Rf: 0.36 cyclohexane.
IR (CHCl$_3$)
Aromatic 1569, 1583, 1510, 1493 cm$^{-1}$

Preparation 5

1-iodo-4-[[dimethyl(1,1-dimethylethyl)silyl]oxy]-benzene 387 mg of imidazole and 411 mg of tertbutyldimethylsilyl chloride is added at ambient temperature and under an inert atmosphere to 500 mg of para-iodo-phenol in 4 ml of dimethylformamide and the mixture is maintained under agitation for 15 hours at ambient temperature then for 1 hour at 40° C. The reaction medium is poured into water, and the aqueous phase is extracted with dichloromethane. The organic phase is then dried and evaporated under reduced pressure. In this way 636 mg of expected product is obtained.

Rf=0.82 cyclohexane/acetate ethyl 9/1).
NMR (CDCl$_3$) 200 MHz

| | |
|---|---|
| 0.1 p.p.m (s) | CH$_3$ |
| 0.9 p.p.m (s) | tBu |
| 6.55 p.p.m (d) to 7.5 p.p.m (d): | the aromatic 4H's |

Preparation 6

1-iodo-4-(phenylmethoxy)-benzene 2.4 g of 50% sodium hydride in oil is added at 0° C. and under an inert atmosphere to 10 g of para-iodo-phenol in 150 ml of dimethylformamide, the mixture is maintained under agitation for 30 minutes and 5.9 ml of benzyl bromide is added. After agitation for 30 minutes while allowing the reaction medium to return to ambient temperature, the reaction medium is poured onto ice and a precipitation of the product is observed. After drying, 14.7 g of expected product is obtained.

Rf=0.67 cyclohexane/ethyl acetate 9/1).
NMR (CDCl$_3$) 200 MHz

| | |
|---|---|
| 7.35 (m) | aromatic H's of the benzyl |
| 7.5 (d) 2 H | H$_2$ and H$_6$ |
| 6.7 (d) 2 H | H$_3$ and H$_5$ |
| 5 (s) | C$\underline{H}_2$Ph |

Preparation 7

3,5-dibromo-4-[[(trifluoromethyl) sulphonyl]oxy]-benzaldehyde 14.73 ml of triflic anhydride is added, under inert gas and at 0° C., to 19.0 g of 3,5-dibromo-4-hydroxy-benzaldehyde in 100 ml of pyridine. Agitation is carried out for 1 hour while allowing the temperature to return to ambient, the reaction medium is poured into water and the aqueous phase is extracted with 3 times 150 ml of dichloromethane. The organic phases are dried and evaporated to dryness under reduced pressure. 23.83 g of crude product is obtained which is purified by filtration chromatography using a cyclohexane/ethyl acetate mixture 1/1 as eluant. In this way 23.83 g of expected product is obtained. Rf: 0.71, cyclohexane/ethyl acetate 1/1. The operation is carried out in an equivalent manner for the preparation of the following triflates of general formula II

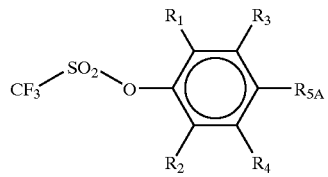

| Preparation | $R_1$ | $R_3$ | $R_2$ | $R_4$ | $R_{5a}$ | Rf | $C_6H_{12}$/AcOEt |
|---|---|---|---|---|---|---|---|
| 8 | Me | H | Me | H | CHO | 0.34 | 9/1 |
| 9 | H | Me | iPr | H | $COCH_3$ | 0.64 | 7/3 |
| 10 | iPr | H | Cl | Me | $COCH_3$ | 0.44 | 7/3 |
| 11 | Cl | H | OMe | H | CHO | 0.29 | 8/2 |
| 12 | Cl | H | Cl | H | CHO | 0.53 | 7/3 |
| 13 | iPr | H | Cl | H | CHO | 0.35 | 9/1 |
| 14 | H | H | Cl | H | $CO_2Me$ | 0.74 | 7/3 |
| 15 | CH=CH—CH=CH | | Cl | H | CHO | 0.75 | 7/3 |
| 16 | Cl | H | $CF_3$ | H | CHO | 0.22 | 9/1 |

EXAMPLE 1

2,6-dibromo-4'-hydroxy-(1,1'-biphenyl)-4-carboxaldehyde

Stage A: Coupling 2,6-dibromo-4'-methoxy-(1,1'-biphenyl)-4-carboxaldehyde 50 ml of toluene, 20 ml of ethanol, 6.6 ml of 2M sodium carbonate, 534 mg of (4-methoxyphenyl)-boronic acid obtained as in Preparation 1, 245 mg of LiCl, 112 mg of Tetrakis (triphenylphosphine)-palladium(0) are added, under inert gas, to 1.32 g of the triflate obtained in Preparation 7, and agitation is carried out under reflux for 1 hour 30 minutes. After dilution with ethyl acetate the organic phase is washed with 2N soda, then with a saturated solution of NaCl, dried then evaporated under reduced pressure, followed by purification by chromatography on silica eluting with a cyclohexane-ethyl acetate mixture(98-2) and 89 mg of expected product is obtained.

Rf=0.68 cyclohexane/ethyl acetate (7/3))

NMR ($CDCl_3$, 300 MHz)

| 3.88 (s) | $OC\underline{H}_3$ |
|---|---|
| 7.01–7.15 (AA' BB') | Ph—O— |
| 8.12 | $H_3, H_5$ |
| 9.94 (s) | CHO |

Stage B: Deprotection 2,6-dibromo-4'-hydroxy-(1,1'-biphenyl)-4-carboxaldehyde 15 ml of dichloromethane is added under inert gas to 1.2 g of the product prepared in the previous stage, then, at −45° C., 0.75 ml of $BBr_3$ is added and agitation is carried out for 1 hour at −45° C. then for 15 hours while allowing the temperature to evolve from −45° C. to −22° C. After hydrolysis by the addition of a saturated solution of sodium acetate and extraction with dichloromethane and ethyl acetate, the organic phase is dried and evaporated under reduced pressure. The crude reaction product is chromatographed on silica eluting with a cyclohexane-ethyl acetate mixture (98-2). In this way 471 mg of expected product is obtained.

Rf=0.28 cyclohexane/ethyl acetate (8/2)

I.R. Nujol

OH/NH absorption ~3450 $cm^{-1}$

C=O 1684 $cm^{-1}$

Aromatic 1611, 1589, 1534, 1518 $cm^{-1}$

NMR ($CDCl_3$, 300 MHz)

4.97 (s, OH); 6.95 and 7.20 (AA'BB', Ph—O); 8.12 (s) H3, H5;

9.94 (s, CHO).

EXAMPLE 2

2,6-dibromo-4'-hydroxy-(1,1'-biphenyl)-4-methanol 140 mg of the product prepared in Example 1 in 3 ml of methanol is cooled down to 0° C., 15 mg of sodium borohydride is added followed by agitation for 1 hour at 0° C. The methanol is evaporated off under reduced pressure and water is added to the residue. The aqueous phase is extracted with ethyl acetate, and the organic phase is evaporated under reduced pressure. The residue is then chromatographed on silica eluting with a cyclohexane/ethyl acetate mixture 9/1. 47 mg of expected product is obtained.

Rf=0.67 cyclohexane/ethyl acetate (4/6)

I.R. Nujol

Absence of C=O

General absorption OH/NH

Aromatic 1612, 1594, 1518 $cm^{-1}$

NMR ($CDCl_3$, 300 MHz)

1.83 (t, OH); 4.71 (d, $CH_2$); 4.95 (s, OH); 6.92–7.08 (AA'BB', Ph—O); 7.64 (s, H3, H5).

EXAMPLE 3

2-chloro-4'-hydroxy-6-methoxy-(1,1'-biphenyl)-4-methanol

Stage A: Coupling 2-chloro-6-methoxy-4'-phenylmethoxy-(1,1'-biphenyl)-4-carboxaldehyde 1.4 g of potassium bromide, 3.7 g of $K_3PO_4$ monohydrate, 2.68 g then 0.55 g of the boronic acid obtained in Preparation 2, 0.62 g of Tetrakis (triphenylphosphine)-palladium(0) are added to a solution, under an inert atmosphere, of 3 g of the triflate obtained in Preparation 11 in 20 ml of dioxane, and agitation is carried out for 12 hours at 110° C. After filtration then evaporation under reduced pressure, the mixture is chromatographed on silica eluting with a cyclohexane/ethyl acetate mixture 9/1 then 8/2. 762 mg of the expected pure product is obtained.

Rf=0.4 cyclohexane/ethyl acetate 8/2

NMR (CDCl, 250 MHz)

| | |
|---|---|
| 3.82 (s) | OC$\underline{H}_3$ |
| 5.11 (s) | C$\underline{H}_2$Ph |
| 7.08 and 7.25 AA' BB' | Ph—O |
| 7.37 and 7.6 (2d) J = 2.5 | H$_3$, H$_5$ |
| 7.3–7.5 (m) | H of the benzyl |
| 9.95 (s) | C$\underline{H}$O |

Stage B: Deprotection and Reduction
2-chloro-4'-hydroxy-6-methoxy-(1,1'-biphenyl)-4-methanol 200 mg of the product obtained in the previous stage is mixed at ambient temperature in 5 ml of ethanol with 60 mg of palladium on carbon at 9.5%. The medium is placed under hydrogen atmosphere and agitation is carried out for 3 hours at 20° C. followed by filtration then evaporation under reduced pressure in order to obtain 265 mg a brown oil. The mixture is purified by chromatography eluting with a cyclohexane/ethyl acetate mixture 8/2, then 7/3 and finally 1/1. 62 mg of expected product is obtained as well as 37 mg of reduced product (R$_5$=methyl).

Rf=0.1 cyclohexane/ethyl acetate 7/3
NMR (CDCl$_3$ 250 MHz)

| | |
|---|---|
| 1.74 (t) | CH$_2$O$\underline{H}$ |
| 4.71 (d) | C$\underline{H}_2$OH |
| 3.75 (s) | OC$\underline{H}_3$ |
| 4.79 (s) | O$\underline{H}$ |
| 6.9 and 7.16 AA' BB' | Ph—O |
| 6.91 and 7.09 2d | H$_3$, H$_5$ |

EXAMPLE 4

2-chloro-4'-hydroxy-6-(1-methylethyl)-(1,1'-biphenyl)-4-methanol

The process is carried out in an equivalent manner to Example 3 Stage A and B (coupling+deprotection) as in Example 2 (reduction) starting with 210.9 mg of the triflate obtained in Preparation 13 and 36 mg of expected product is obtained.

Rf=0.32 cyclohexane/ethyl acetate 7/3
NMR (CDCl$_3$ 300 MHz)

| | |
|---|---|
| 1.09 (d) | CH(C$\underline{H}_3$)$_2$ |
| 2.81 (sept) | C$\underline{H}$(CH$_3$)$_2$ |
| 4.60 (s) | C$\underline{H}_2$OH |
| 7.28 (m) | H$_3$, H$_5$ |
| 6.88 and 6.94 AA' BB' | Ph—O |

EXAMPLE 5

2-chloro-4'-hydroxy-(1,1'-biphenyl)-4-methanol
Stage A: Coupling
Methyl 2-chloro-4'-phenylmethyloxy-(1,1'-biphenyl)-4-carboxylate The operation is carried out in an equivalent manner to Example 3 Stage A starting with 1.58 g of the triflate obtained in Preparation 14 and 0.96 g of expected product is obtained.

Rf=0.42 cyclohexane/ethyl acetate 90/10
NMR (CDCl$_3$ 300 MHz)

| | |
|---|---|
| 3.95 s | CO$_2$C$\underline{H}_3$ |
| 5.12 s | PhC$\underline{H}_2$ |
| 8.13 d | H$_3$ |
| 7.95 dd | H$_5$ |
| 7.30 7.50 m 6 H | H of the benzyl + H$_6$ |
| 7.04 and 7.41 AA' BB' | Ph—O |

Stage B: Reduction of the Ester
2-chloro-4'-phenylmethyloxy-(1,1'-biphenyl)-4-methanol 204.4 mg of the ester in 10 ml of tetrahydrofuran and 44 mg of lithium and aluminium hydride are mixed together for 2 hours, under an inert atmosphere and at 0° C., then the mixture is poured into a saturated solution of sodium bicarbonate. After extraction with ethyl acetate, drying and evaporation under reduced pressure, 174 mg of expected product is obtained.

Rf=0.17 cyclohexane/ethyl acetate 8/2.
Stage C: Deprotection
2-chloro-4'-hydroxy-(1,1'-biphenyl)-4-methanol The operation is carried out in an equivalent manner to Example 3 Stage B starting with 174 mg of the benzyl derivative of the previous stage and 55 mg of expected product and 37% of the reduced analogue are obtained (R$_5$=CH$_3$, Rf=0.53 cyclohexane/ethyl acetate 7/3)
Rf=0.18 cyclohexane/ethyl acetate 7/3
NMR DMSO 250 MHz

| | |
|---|---|
| 4.52 s | C$\underline{H}_2$OH |
| 5.33 s | CH$_2$O$\underline{H}$ |
| 7.30 ws 2 H and 7.44 s 1 H | H$_3$, H$_5$, H$_6$ |
| 6.84 d and 7.23 d | Ph—O |
| 9.59 s | Ph—O$\underline{H}$ |

EXAMPLE 6

4'-ethyl-5'-methyl-2'-(1-methylethyl)-(1,1'-biphenyl)-4-ol

The operation is carried out in an equivalent manner to Example 4 starting with 1.52 g of the triflate obtained in Preparation 9. After purification by chromatography, eluting with a cyclohexane/ethyl acetate mixture 10/0, 9/1 then 7/3, 100 mg of expected product is obtained which is recrystallized from pentane, as well as 48 mg of the corresponding alcohol (R$_5$=CH(OH)CH$_3$, Rf=0.27).

Rf=0.55 cyclohexane/ethyl acetate: 1/1
M.p.=106–108° C.
NMR (CDCl$_3$)

| | |
|---|---|
| 1.15 d | CH(C$\underline{H}_3$)$_2$ |
| 1.26 d | C$\underline{H}_2$CH$_3$ |
| 2.66 d | CH$_2$C$\underline{H}_3$ |
| 2.28 s | C$\underline{H}_3$ |
| 3.03 d | C$\underline{H}$(CH$_3$)$_2$ |
| 4.71 s | OH |
| 6.85 and 7.15 2d | Ph—O |
| 7.14 and 6.95 2s | H$_3$' and H$_6$' |

EXAMPLE 7

2-chloro-4'-hydroxy-6-(trifluoromethyl)-(1,1'-biphenyl)-4-methanol

The process is carried out in an equivalent manner to Example 3 starting with 285 mg of the triflate obtained in Preparation 16 and 10.6 mg of expected product is obtained.

Rf=0.23 cyclohexane/ethyl acetate: 7/3
NMR (DMSO, 300 MHz)

| | |
|---|---|
| 4.62 d | C$\underline{H}_2$OH |
| 5.54 t | CH$_2$O$\underline{H}$ |
| 6.82 and 6.98 AA' BB' | Ph-OH |
| 7.72 ws 7.76 ws | H$_3$, H$_5$ |
| 9.62 s | Ph—O$\underline{H}$ |

EXAMPLE 8

3-chloro-4-(4-hydroxyphenyl)-1-naphthalene-methanol

Stage A: Coupling
3-chloro-4-(4-phenylmethoxyphenyl)-1-naphthalene-carboxaldehyde.

The process is carried out in an equivalent manner to Example 3 Stage A starting with 1.7 g of the triflate obtained in Preparation 15 and 1.1 g of the expected purified product is obtained.

Rf=0.50 cyclohexane/ethyl acetate: 8/2
Infrared spectrum (IR) Solvent: CHCl$_3$
1693 cm$^{-1}$ carbonyle
1609, 1576, 1563, 1516, 1506cm$^{-1}$ aromatics Stage B: Deprotection
3-chloro-4-(4-hydroxyphenyl)-1-naphthalene-carboxaldehyde (product a) and 3-chloro 4-[4-hydroxy 3-(phenylmethyl) phenyl] 1-naphthalene carboxaldehyde (product b).

150 mg of the chlorinated derivative of the previous stage and 3 ml of trifluoroacetic acid are mixed together for 10 minutes under an inert atmosphere. After extraction with ethyl acetate and evaporation under reduced pressure, the crude product is purified by chromatography eluting with a cyclohexane-dichloromethane/ether mixture 70/20/10. 40 mg. of expected product (a) is obtained which is used as it is in the following stage as well as 60 mg of the analogue (b) deprotected and rearranged in position 3 of the phenyl (Rf=0.45 cyclohexane/ethyl acetate 70/30).

Rf=0.40 cyclohexane/ethyl acetate: 7/3

Stage C: Reduction
3-chloro-4-(4-hydroxyphenyl)-1-naphthalene-methanol

The process is carried out in an equivalent manner to Example 2, starting with product (a) obtained in the previous stage. 25 mg of the expected pure product is obtained.

Rf=0.15 cyclohexane/ethyl acetate: 7/3

| Microanalysis | | | | |
|---|---|---|---|---|
| % found | C 71.6 | H 4.50 | Cl 12.5 | |
| % calculated | C 71.71 | H 4.6 | Cl 12.45 | O 11.24 |

EXAMPLE 9

4-[4-hydroxy-3-(phenylmethyl)phenyl]-3-chloro-1-naphthalenemethanol

The operation is carried out in an equivalent manner to Example 3, starting with 60 mg of product (b) obtained in Example 8 Stage B and 40 mg of expected product is obtained.

Rf=0.15 (cyclohexane/ethyl acetate 70/30
NMR (CDCl$_3$)
1.82 CH$_2$O$\underline{H}$
5.18 (s) C$\underline{H}_2$OH
4.07 (s) C$\underline{H}_2$Ph
4.82 (s) Ph—O$\underline{H}$
6.94 (d1) 1H; 7.10 (m) 2H; 7.15 to 7.47 5H; 7.42 1H; 7.53 2H;
7.69 (s) 1H; 8.09 (d) 1H: Aromatics

EXAMPLE 10

4-(2-chloro-4-methyl-1-naphthalenyl)-phenol 190 mg of the alcohol obtained in Stage C of Example 8, 50 mg of palladium on carbon at 9.5 % and 30 ml of ethyl acetate are mixed together for 15 minutes under a hydrogen atmosphere at ambient temperature. After filtration and evaporation under reduced pressure, the crude product is purified by chromatography eluting with a cyclohexane/ethyl acetate mixture 95/5. In this way 45 mg of expected product is obtained.

Rf=0.60 (cyclohexane/ethyl acetate)
NMR (CDCl3, 250 MHz)
2.71 s C$\underline{H}_3$
5.14 s Ph—O$\underline{H}$
6.98 and 7.20 Ph—OH
7.25 to 7.40, 7.99 dd naphthyl

| Microanalysis | | | | |
|---|---|---|---|---|
| % found | C 75.7 | H 5.0 | Cl 13.2 | |
| % calculated | C 75.98 | H 4.88 | Cl 13.19 | O 5.95 |

EXAMPLE 11

2,6-dimethyl-4'-hydroxy-(1,1'-biphenyl)-4-carboxaldehyde

Stage A: Coupling
2,6-dimethyl-4'-[[(1,1-dimethylethyl)diphenylsilyl]oxy](1,1'-biphenyl)-4-carboxaldehyde 1.58 g of LiCl, 600 mg Tetrakis(triphenylphosphine)-palladium(0), 10.56 g of [4-[[(1,1-dimethylethyl) diphenylsilyl] oxy]phenyl]-tributyltin obtained in Preparation 4 is added, under inert gas, to 4 g of the triflate obtained in Preparation 8 in 20 ml of dioxane, and agitation is carried out at 100° C. for 16 hours. The dioxane is partially evaporated followed by taking up in dichloromethane. The organic phase is washed with a saturated solution of KF, dried then evaporated under reduced pressure. The residue is purified by chromatography on silica eluting with a cyclohexane-ethyl acetate mixture (99-01). The expected product is obtained with a yield of 40%.

Rf=0.39 cyclohexane/ethyl acetate (95/5))
IR (CHCl$_3$)
C=O 1693 cm$^{-1}$
aromatics 1607, 1591, 1571, 1510 cm$^{-1}$ Stage B: Deprotection
2,6-dimethyl-4'-hydroxy-(1,1'-biphenyl)-4-carboxaldehyde 35 ml of tetrabutylammonium fluoride is added, under inert gas, to a solution of 1.8 g of the previous product in 10 ml of tetrahydrofuran and agitation is carried out for 10 minutes at ambient temperature. After evaporation of the tetrahydrofuran the crude product thus recovered is chromatographed on silica eluting with a cyclohexane/ethyl acetate mixture (90/10). In this way 634 mg of expected product is obtained.

Rf=0.36 cyclohexane/ethyl acetate 7/3
I.R. CHCl$_3$
OH 3597 cm$^{-1}$
C=O 1695 cm$^{-1}$
aromatics 1613, 1603, 1592, 1568, 1518 cm$^{-1}$

EXAMPLE 12

1-[2-chloro-4'-hydroxy-3-methyl-6-(1-methylethyl)-(1,1'-biphenyl-4-yl)]-ethanone 1.63 g of the boronic acid obtained in Preparation 3, 1.42 g of tri-potassium phosphate 1-hydrate, 538 mg of anhydrous potassium bromide and 474 mg of Tetrakis (triphenylphosphine)-palladium (0) are added, under inert gas, to 1.47 g of the triflate obtained in Preparation 10 in 30 ml of dioxane. Agitation is carried out at 100° C. for 48 hours, the reaction mixture is filtered and evaporated under reduced pressure until a dry extract is obtained. The crude product thus recovered is redissolved in 20 ml of tetrahydrofuran and 4.5 ml of a 1M solution of tetrabutylammonium bromide is added. After agitation for 2 hours the mixture is chromatographed on silica eluting with a cyclohexane/ethyl acetate mixture 1/9 then 4/6. 552 mg of expected crude product is thus collected which is recrystallized from an ether/hexane mixture 1/4. 415 mg of expected purified product is obtained.

Rf=0.15 cyclohexane/ethyl acetate 9/1
M.p.=176–7° C.
NMR (CDCl$_3$) 300 MHz

| | |
|---|---|
| 1.09 (d) | CH(CH$_3$)$_2$ |
| 2.48 and 2.61 (2s) | COCH$_3$ and CH$_3$ |
| 2.75 (m) | CH(CH$_3$)$_2$ |
| 4.88 (s) | Ph—OH |
| 6.92 and 7.02 (2d) aromatics | Ph—O |
| 7.39 (s) aromatics | Ph—CO |

EXAMPLE 13

1-[2-chloro-4'-hydroxy-3-methyl-6-(1-methylethyl)-(1,1'-biphenyl-4-yl)]-ethanol

By operating as in Example 2, starting with 220 mg of the product prepared in Example 12 and after purification by chromatography on silica with a cyclohexane/ethyl acetate mixture 7/3 followed by recrystallization from ether, 152 mg of expected product is obtained.

Rf=0.32 cyclohexane/ethyl acetate 1/1
M.p.=220–222° C.
NMR (CDCl$_3$) 300 MHz

| | |
|---|---|
| 1.10 (d) | CH(CH$_3$)$_2$ |
| 1.52 d | CH(OH)CH$_3$ |
| 2.39 s | Ph—CH$_3$ |
| 2.71 (m) | CH(CH$_3$)$_2$ |
| 4.73 s | Ph—OH |
| 5.21 m | CH(OH)CH$_3$ |
| 1.77 d | CH(OH)CH$_3$ |

EXAMPLE 14

2,6-dichloro-alpha-ethynyl-4'-hydroxy-(1,1'-biphenyl)-4-methanol

Stage A: Coupling
2,6-dichloro-4'-[[(1,1-dimethylethyl)diphenylsilyl]oxy]-(1,1'-biphenyl)-4-carboxaldehyde.

The operation is carried out in an equivalent manner to Example 3 starting with 20.2 g of the triflate obtained in Preparation 12 in 125 ml of dioxane and 22.4 g of the boronic acid obtained in Preparation 3. After purification by chromatography eluting with a cyclohexane/methylene chloride mixture 92/8 then 90/10 and finally 80/20, 12.5 g of a mixture constituted by 62% of dichlorinated product and 38% of monochlorinated product.

Rf=0.66 cyclohexane/ethyl acetate 7/3

Stage B: Addition of Magnesium Compound
2,6-dichloro-alpha-ethynyl-4'-[[(1,1-dimethylethyl)diphenylsilyl]oxy]-(1,1'-biphenyl)-4-methanol 1.5 ml of ethynylmagnesium bromide in THF is added at 0–5° C., to a solution under inert gas of 700 mg of the silylated product prepared in the previous stage in 15 ml of THF, followed by agitation for 2 hours 30 minutes at this temperature. After neutralization with saturated ammonium chloride, extraction is carried out with ethyl acetate, followed by drying, filtering and evaporation under reduced pressure until 720 mg of expected crude product is obtained.

Stage C: Deprotection of the Silylated Product
2,6-dichloro-alpha-ethynyl-4'-hydroxy-(1,1'-biphenyl)-4-methanol The operation is carried out in an equivalent manner to Example 11 Stage B and 90 mg of purified product is obtained.

Rf=0.36 cyclohexane/ethyl acetate: 1/1
NMR (CDCl$_3$ 250 MHz)

| | |
|---|---|
| 2.75 (d) | CH(OH)—C≡C—H |
| 5.47 (ws, d after exchange) | CH(OH)—C≡C—H |
| 2.32 (m) and 4.92 (m) | mobile 2 H's |
| 6.93 and 7.14 AA' BB' | Ph—O |
| 7.59 (s) | H$_3$; H$_5$ |

EXAMPLE 15

2,6-dichloro-alpha-phenyl-4'-hydroxy-(1,1'-biphenyl)-4-methanol

The operation is carried out in an equivalent manner to Example 14 stages B and C by the action of phenyl magnesium bromide on 700 mg of the silylated product of Example 14 Stage A and 203 mg of expected product is obtained.

Rf=0.5 cyclohexane/ethyl acetate: 1/1
NMR (CDCl$_3$ 250 MHz)

| | |
|---|---|
| 5.76 (ws, d after exchange) | CH(OH)—Ph |
| 6.17 (mobile d) | |
| 6.81 and 7.01 AA' BB' | Ph—O |
| 7.25 (t) | H$_4$ of the phenyl |
| 7.35 (t) | H$_3$, H$_5$ of the phenyl |
| 7.44 (dl) | H$_2$, H$_6$ of the phenyl |
| 7.5 (s) | H$_3$, H$_5$ |
| 9.61 mobile s | Ph—OH |

EXAMPLE 16

2,6-dichloro-alpha-ethyl-4'-hydroxy-(1,1'-biphenyl)-4-methanol

The operation is carried out in an equivalent manner to Example 14 stages B and C by the action of ethyl magnesium bromide on 1.2 g of the silylated product of Example 14 Stage A, and 21 mg of expected product is obtained.

Rf=0.47 cyclohexane/ethyl acetate: 1/1
NMR (CDCl$_3$ 250 MHz)

| | |
|---|---|
| 0.87 t | $CH_2\underline{CH}_3$ |
| 1.63 m | $\underline{CH}_2CH_3$ |
| 4.5 m | $C\underline{H}OH$ |
| 5.39 d | $CHO\underline{H}$ |
| 6.83 and 7.03 AA' BB' | Ph—O |
| 7.45 | $H_3, H_5$ |
| 9.62 s | Ph—O$\underline{H}$ |

EXAMPLE 17

3-(2,6-dichloro-4'-hydroxy-(1,1'-biphenyl)-4-yl)-2-propenol

Stage A: Homologation by Phosphine
3-(2,6-dichloro-4'-[[(1,1-dimethylethyl)diphenylsilyl]oxy](1,1'-biphenyl)-4-propenal 1.03 g of triphenylphosphine ($\Phi_3P=CH-CHO$) is added to a solution under inert gas of 1.7 g of the silylated product prepared in Example 14 Stage A, in 1.5 ml of chloroform, and the reaction medium is taken to reflux for 6 hours at 120° C. After cooling down, filtering and evaporation under reduced pressure, the crude product obtained is purified by chromatography, eluting with a cyclohexane/ethyl acetate mixture 9/1. 980 mg of expected product is obtained.

Stage B: Reduction of the Aldehyde
3-(2,6-dichloro-4'-[[(1,1-dimethylethyl)diphenylsilyl]oxy](1,1'-biphenyl)-4-propenol The homologous silylated product obtained in the previous stage is dissolved in 10 ml of methanol. 35 mg of sodium borohydride is added followed by agitation for 1 hour at ambient temperature under an inert atmosphere. The solution is used as it is in the following stage.

Stage C: Deprotection of the Silylated Derivative
3-(2,6-dichloro-4'-hydroxy-(1,1'-biphenyl)-4-yl)-2-propenol 3.5 ml of TBAF is added to the previous solution and the mixture is agitated under an inert atmosphere for 15 minutes. After treatment with a 6N hydrochloric acid solution, extraction with ethyl acetate, drying of the organic phases and evaporation under reduced pressure, 730 mg of expected crude product is obtained which is purified by chromatography eluting with a cyclohexane/ethyl acetate mixture 9/1 then 1/1. 1.27 mg of expected pure product is obtained.

Rf=0.24 cyclohexane/ethyl acetate 1/1
NMR (CDCl$_3$)

| | |
|---|---|
| 1.51 (t, mobile) | $CH=CH-CH_2-O\underline{H}$ |
| 4.37 (m, d after exchange) | $CH=CH-\underline{CH}_2-OH$ |
| 4.85 mobile s | Ph—O$\underline{H}$ |
| 6.41 dt J = 16 | $CH=C\underline{H}-CH_2-OH$ |
| 6.56 wd J = 16 | $C\underline{H}=CH-CH_2-OH$ |
| 6.92 and 7.15 AA' BB' | Ph—O |
| 7.4 s | $H_3, H_5$ |

EXAMPLE 18

2-bromo-4'-hydroxy-6-nitro-(1,1'-biphenyl)-4-methanol

Stage A: Coupling
Methyl 2,6-dinitro-4'-[[(1,1-dimethylethyl) dimethylsilyl]oxy]-(1,1'-biphenyl)-4-carboxylate 1.53 g of methyl 4-chloro-3,5-dinitro benzoate obtained in Example 30 Stage A in 15 ml of tetrahydrofuran is mixed under an inert atmosphere with 1.96 g of the product of Preparation 5 and 2.8 g of copper, then agitation is carried out for 24 hours at 120° C. After filtration, evaporation is carried out under reduced pressure and the crude product is purified by chromatography eluting with a cyclohexane/ethyl acetate mixture 9/1 then 1/1. In this way 1.2g of expected product is obtained (Rf=0.45 cyclohexane/ethyl acetate 7/3)

IR (CHCl$_3$)
C=O 1735cm$^{-1}$
Aromatics+NO$_2$: 1620, 1607, 1575, 1545, 1517 cm$^{-1}$ Stage B: Reduction of the Nitro Group
Methyl 2-amino-4'-[[(1,1-dimethylethyl)dimethylsilyl]oxy]-(1,1'-biphenyl)-6-nitro-4-carboxylate The mixture constituted by 1.15 g of the product obtained in the previous stage, 4.9 ml of cyclohexene and 345 mg of Pd(OH)$_2$ is agitated for 16 hours under an inert atmosphere, under reflux. After filtration then evaporation under reduced pressure, the crude product is purified by chromatography eluting with a cyclohexane/ethyl acetate mixture 9/1. 670 mg of an oil is obtained which is crystallized from an ethyl ether/hexane mixture. In this way 522 mg of expected product is obtained.

Rf=0.2 cyclohexane/ethyl acetate 85/15
IR (CHCl$_3$)

| | |
|---|---|
| =C—NH$_2$ | 3500 cm$^{-1}$ |
| C=O | 1726 cm$^{-1}$ |
| Aromatics | 1621 cm$^{-1}$ |
| 1st band NO$_2$ | 1610 cm$^{-1}$ |
| NH$_2$ | 1635, 1516 cm$^{-1}$ |

Stage C: Substitution of NH$_2$ by Br
Methyl 2-bromo-4'-[[((1,1-dimethylethyl)dimethylsilyl]oxy]-(1,1'-biphenyl)-6-nitro-4-carboxylate 0.062 ml of terbutylnitrite is added under an inert atmosphere to a mixture cooled down to −5° C., constituted by the product of the previous stage in 1.3 ml of tribromomethyl. After agitation for 15 minutes at 100° C., the reaction medium is evaporated under reduced pressure and the crude reaction product is purified by chromatography eluting with a cyclohexane/ethyl acetate mixture 95/05. In this way 81 mg of the expected pure product is obtained.

Rf=0.33 cyclohexane/ ethyl acetate 9/1
IR (CHCl$_3$)
Absence of =C—NH$_2$

| | |
|---|---|
| C=O | 17.30, 1436 cm$^{-1}$ |
| Aromatic | 1608, 1572 cm$^{-1}$ |
| 1st band NO$_2$ | 1537, 1516 cm$^{-1}$ |

Stage D: Deprotection
Methyl 2-bromo-4'-hydroxy-6-nitro-(1,1'-biphenyl)-4-carboxylate The operation is carried out in an equivalent manner to Example 11 Stage B starting with the product obtained in the previous stage. 279 mg of the desilylated product is obtained which is used as it is in the following stage.

Rf=0.38 cyclohexane/ethyl acetate: 9/1

Stage E: Reduction
2-bromo-4'-hydroxy-6-nitro-(1,1'-biphenyl)-4-methanol

The operation is carried out in an equivalent manner to Example 5 Stage B starting with 110 mg of the product prepared in the previous stage. In this way 85 mg of expected product is obtained which is recrystallized from ethyl ether.

Rf=0.18 cyclohexane/ethyl acetate: 7/3

| Microanalysis | | | | |
|---|---|---|---|---|
| % found | C 48.2 | H 2.9 | N 4.1 | Br 24.8 |
| % calculated | C 48.2 | H 3.1 | N 4.3 | Br 24.7 |

EXAMPLE 19

2-amino-6-bromo-4'-hydroxy-(1,1'-biphenyl)-4-methanol

Stage A: Reduction $NO_2$+Deprotection

Methyl 2-amino-6-bromo-4'-hydroxy-(1,1'-biphenyl)-4-carboxylate

The process is carried out in an equivalent manner to Example 18 Stage B starting with 10 g of the product obtained in Stage C of the same example. 7.97 g of expected product (reduced and deprotected) and 577 mg of the protected analogue are obtained (Rf=0.56 cyclohexane/ethyl acetate 7/3).

Rf=0.17 cyclohexane/ethyl acetate 7/3

Stage B: Reduction of the Ester 2-amino-6-bromo-4'-hydroxy-(1,1'-biphenyl)-4-methanol The operation is carried out in an equivalent manner to Example 5 Stage B starting with 550 mg of the product obtained in the previous stage. 250 mg of expected product is obtained.

Rf=0.18 cyclohexane/ethyl acetate 7/3

| Microanalysis | | | | |
|---|---|---|---|---|
| % found | C 52.8 | H 4.1 | N 4.5 | Br 26.9 |
| % calculated | C 53.1 | H 4.1 | N 4.8 | Br 27.2 |

IR (Nujol)

Absence of C=O

OH/NH absorption

Aromatic region, $NH_2$: 1606, 1586, 1550, 1540, 1516, 1496 $cm^{-1}$

EXAMPLE 20

2-bromo-4'-hydroxy-6-methylthio-(1,1'-biphenyl)-4-methanol

Stage A: Substitution of $NH_2$ by SMe

Methyl 2-bromo-4'-[[(1,1-dimethylethyl)diphenylsilyl]oxy]-6-methylthio-(1,1'-biphenyl)-4-carboxylate The mixture constituted by 400 mg of the product prepared in Example 19 Stage A (reduced and protected product) in 1 ml of chloroform, 0.17 ml of $(CH_3S)_2$ and 0.16 ml of terbutylnitrite is agitated for 16 hours under an inert atmosphere at ambient temperature. After hydrolysis of the reaction medium, extraction and concentration under reduced pressure, the crude product is purified by chromatography eluting with a cyclohexane/ethyl acetate mixture 998/02. In this way 245 mg of expected product is obtained.

Rf=0.47 cyclohexane/ethyl acetate 1/1

NMR (CDCl, 200 MHz)

| | |
|---|---|
| 0.19 s | $Si(CH_3)_2$ |
| 0.9 s | Si—$C(CH_3)_3$ |
| 2.3 s | S—$CH_3$ |
| 6.85 and 7.0 AA' BB' | Ph—O |
| 7.68 d and 8.0 d | $H_3$, $H_5$ |

Stage B: Reduction+Deprotection 2-bromo-4'-hydroxy-6-methylthio-(1,1'-biphenyl)-4-methanol The operation is carried out in an equivalent manner to Example 18 stages D and E starting with 200 mg of the product obtained in the previous stage. 10.9 mg of expected pure product is thus obtained.

Rf=0.2 cyclohexane/ethyl acetate 7/3

NMR (DMSO, 250 MHz)

| | |
|---|---|
| 2.31 s | S—$CH_3$ |
| 4.53 s | $CH_2$OH |
| 5.34 (t, mobile) | $CH_2OH$ |
| 6.81 and 6.93 AA' BB' | Ph—O |
| 7.17 (ws) and 7.39 (ws) | $H_3$, $H_5$ |
| 9.54 (s, l) | Ph—OH |

EXAMPLE 21

2-bromo-4'-hydroxy-6-(1H-pyrrol-1-yl)-(1,1'-biphenyl)-4-methanol

Stage A: Formation of the Pyrrol Starting with the Amine

Methyl 2-bromo-4'-[[(1,1-dimethylethyl)diphenylsilyl]oxy]-6-(1H-pyrrol-1-yl)-(1,1'-biphenyl)-4-carboxylate 700 mg of the product prepared in Example 19 (reduced and protected product) in 17 ml of acetic acid and 23 ml of 2,6-dimethoxy tetrahydrofuran are mixed under an inert atmosphere and taken to reflux for 16 hours. After hydrolysis of the reaction medium, extraction with ethyl acetate and evaporation under reduced pressure, 813 mg of expected crude product is obtained which is used as it is for the following stage.

Rf=0.8 cyclohexane/ethyl acetate

NMR ($CDCl_3$, 200 MHz)

| | |
|---|---|
| 0.12 s | $Si(CH_3)_2$ |
| 0.85 s | Si—$C(CH_3)_3$ |
| 3.85 s | $CO_2CH_3$ |
| 5.95 m | $H_3$, $H_4$ of the pyrrol |
| 6.56 m | $H_2$, $H_5$ of the pyrrol |
| 6.66 and 6.87 | AA' BB' Ph—O |
| 7.31 and 7.67 | $H_3$, $H_5$ |

Stage B: Reduction and Deprotection 2-bromo-4'-hydroxy-6-(1H-pyrrol-1-yl)-(1,1'-biphenyl)-4-methanol The operation is carried out in an equivalent manner to Example 18 stages D and E starting with 750 mg of the product obtained in the previous stage. In this way 212 mg of expected pure product is obtained.

Rf=0.29 cyclohexane/ethyl acetate 7/3

NMR (DMSO, 250 MHz)

| | |
|---|---|
| 5.42 t, mobile | $CH_2OH$ |
| 4.57 d, s after exchange | $CH_2OH$ |

| | |
|---|---|
| 5.95 m | $H_3$, $H_4$ of the pyrrol |
| 6.56 m | $H_2$, $H_5$ of the pyrrol |
| 6.66 and 6.87 AA' BB' | Ph—OH |
| 7.31 and 7.67 d | $H_3$, $H_5$ |
| 9.44 s mobile | Ph—O$\underline{H}$ |

EXAMPLE 22

2,6-dimethoxy-4'-hydroxy-(1,1'-biphenyl)-4-methanol

Stage A: Coupling
2,6-dimethoxy-4'-benzyloxy-(1,1'-biphenyl)-4-carboxaldehyde 19 g of the boronic acid obtained in Preparation 2, 7.15 g of tripotassium phosphate 1-hydrate and 1.2 g of Tetrakis (triphenylphosphine)-palladium(0) are added, under inert gas, to 5.07 g of 4-bromo-3,5-dimethoxy-benzaldehyde (Finorga) in 50 ml of dioxane. The reaction mixture is taken to reflux for 15 hours, poured into ice-cooled water and the aqueous phase is extracted with ether then ethyl acetate. The organic phases are dried and evaporated under reduced pressure. The crude product thus recovered is chromatographed on silica eluting with a dichloromethane/pentane mixture 70/30. In this way 2.84 g of expected product is collected.

Rf=0.5 dichloromethane
I.R. $CHCl_3$

| | |
|---|---|
| C=O | 1692 cm$^{-1}$ |
| Aromatics | 1610, 1582, 1572, 1520, 1499 cm$^{-1}$ |

Stage B: Debenzylation and Reduction
2,6-dimethoxy-4'-hydroxy-(1,1'-biphenyl)-4-methanol 502.3 mg of the product obtained in the previous stage in 13 ml of ethyl acetate is mixed at ambient temperature with 161 mg of palladium on carbon at 9.5%. The reaction medium is placed under a hydrogen atmosphere and agitation is carried out for 3 hours. After filtration, the filtrate is evaporated under reduced pressure and the crude residue is chromatographed on silica eluting first with dichloromethane then with a dichloromethane/methanol mixture 95/5. In this way 134 mg of expected product is collected as well as 110 mg of the product of Example 23 ($R_5$=Me).

Rf=0.41 dichloromethane/methanol 9/1
M.p.=184° C.
I.R. Nujol

| | |
|---|---|
| Absence of C=O | |
| OH/NH region | max 3500 cm$^{-1}$ |
| | max 3260 cm$^{-1}$ |
| Aromatics | 1610, 1593, 1579, 1523, 1492 cm$^{-1}$ |

EXAMPLE 23

2',6'-dimethoxy-4'-methyl-(1,1'-biphenyl)-4-ol 106.5 mg of the product obtained in Stage A of Example 22 in 3.5 ml of ethyl acetate is mixed at ambient temperature with 34 mg of palladium on carbon at 9.5%. The reaction medium is placed under a hydrogen atmosphere and agitation is carried out for 24 hours at 20° C. After filtration, the mixture is evaporated under reduced pressure and in this way 69 mg of expected product is collected.

Rf=0.45 cyclohexane/ethyl acetate 7/3
M.p.=162° C.
I.R. Nujol

| | |
|---|---|
| Absence of C=O | |
| —OH | 3598 cm$^{-1}$ |
| Aromatics | 1606, 1592, 1575, 1521, 1489 cm$^{-1}$ |

EXAMPLE 24

2,6-dichloro-4'-hydroxy-(1,1'-biphenyl)-4-methanol

Stage A: Protection
2-(3,5-dichlorophenyl)-1,3-dioxolane 4.66 g of 3,5-dichlorobenzaldehyde is mixed with 0.23 g of paratoluenesulphonic acid, 3 ml of ethylene glycol and 40 ml of toluene. The reaction medium is heated under reflux for 2 hours, poured into a saturated solution of sodium bicarbonate and the aqueous phase is decanted. The organic phase is dried and evaporated under reduced pressure. 5.756 g of expected product is isolated in the form of an oil.

Rf=0.45 cyclohexane/ethyl acetate 9/1.
I.R. $CHCl_3$

| | |
|---|---|
| Absence of C=O | |
| Aromatics | 1592, 1575 cm$^{-1}$ |

Ketal
Stage B: Orthometallation and Iodation
2-(3,5-dichloro-4-iodo phenyl)-1,3-dioxolane A solution of 5.631 g of the product obtained in the previous stage in 45 ml of tetrahydrofuran is cooled down to −78° C. under an inert atmosphere, 21.4 ml of a solution of n-butyllithium is added dropwise over 1 hour, the mixture is agitated at −78° C. for 30 minutes, then a solution of 6.94 g of N-iodosuccinimide in 40 ml of tetrahydrofuran is added dropwise over 1 hour. Agitation is carried out for 1 hour at −78° C., the reaction mixture is poured into a saturated solution of ammonium chloride and extracted with methylene chloride. The organic phase is dried and evaporated under reduced pressure. 10.11 g of expected product is isolated in the form of an oil.

Rf=0.22 cyclohexane/ethyl acetate 95/5.

Stage C: Coupling
2-[2,6-dichloro-4'-phenylmethoxy-(1,1'-biphenyl)-4-yl]-1,3-dioxolane 10.11 g of the product obtained in the previous stage is mixed with 60 ml of toluene, 10.69 g of boronic acid (Preparation 2), 29.3 ml of a solution (2M) of sodium carbonate, 15 ml of ethanol and 1.69 g of Tetrakis (triphenylphosphine)-palladium (0). Agitation is carried out under toluene reflux under an inert atmosphere for 15 hours and the reaction mixture is poured into a saturated solution of sodium bicarbonate and extracted with ether. The organic phase is washed with a saturated solution of ammonium chloride, then with a solution of sodium chloride, dried and evaporated under reduced pressure. 14.43 g of expected product is isolated in the form of an oil.

Rf=0.2 cyclohexane/ethyl acetate 90/10.
I.R. $CHCl_3$
Aromatics 1611, 1580, 1555, 1520, 1498 cm$^{-1}$ Stage D: Deprotection (Hydrolysis of Ketal)
2,6-dichloro-4'-phenylmethoxy-(1,1'-biphenyl)-4-carboxaldehyde 14.31 g of the product obtained in the previous stage is mixed with 70 ml of tetrahydrofuran and 36 ml of 1N hydrochloric acid. The reaction mixture is heated under tetrahydrofuran reflux for 15 hours and treated with a saturated solution of sodium bicarbonate and the aqueous phase is extracted with dichloromethane. The organic phase is dried and evaporated under reduced pressure. 13.24 g of crude product in the form of an oil is chromatographyed on silica eluting with a cyclohexane/ethyl acetate mixture 99.5/0.5. In this way 2.352 g of expected product is obtained.

Rf=0.4 cyclohexane/ethyl acetate 90/10
I.R. CHCl3
Aromatics 1609, 1590, 1577, 1548, 1516 cm$^{-1}$
C=O 1707 cm$^{-1}$ Stage E: Debenzylation
2,6-dichloro-4'-hydroxy-(1,1'-biphenyl)-4-methanol 101.4 mg of the product obtained in the previous stage in 5 ml ethyl acetate is mixed at ambient temperature with 31 mg of palladium on carbon at 9.5%. The reaction medium is placed under a hydrogen atmosphere and agitation is carried out for 4 hours at 20° C. After filtration, the filtrate is evaporated under reduced pressure then purified by chromatography on silica eluting with a cyclohexane/ethyl acetate mixture 9/1. In this way 61 mg of expected product is collected.

Rf=0.21 cyclohexane/ethyl acetate 7/3
M.p.=161° C.
I.R. CHCl$_3$
—OH 3599 cm$^{-1}$
Aromatics 1613, 1603, 1593, 1546, 1520, 1501 cm$^{-1}$

EXAMPLE 25

2,6-dichloro-4'-hydroxy-(1,1'-biphenyl)-4-carboxaldehyde

The mixture constituted by 101.6 mg of the product prepared in Stage D of Example 24 in 1 ml of dichloromethane and 0.053 ml of trimethylsilyl iodide is agitated for 1 hour at 25° C. under an inert atmosphere. After hydrolysis with methanol and evaporation under reduced pressure, the residue is taken up in dichloromethane, washed with water, the organic phase is dried and evaporated under reduced pressure. The crude product obtained is purified by chromatography eluting with a cyclohexane/ethyl acetate mixture 95/5. 50 mg of expected pure product is obtained.

M.p.=154–156° C.
Rf=0.21 cyclohexane/ethyl acetate 8/2
NMR (DMSO 300 MHz)

| 6.88 d and 7.10 AA' BB' | Ph—OH |
| 8.04 s 2 H | H$_3$, H$_5$ |
| 9.77 s | Ph—O$\underline{H}$ |
| 10.00 s | C$\underline{H}$O |

EXAMPLE 26

4'-hydroxy-2.3,5,6-tetrachloro-(1,1'-biphenyl)-4-methanol

Stage A: Coupling
4'-phenylmethoxy-2,3,5,6-tetrachloro-(1,1'-biphenyl)

1 g of 3-iodo-1,2,4,5-tetrachlorobenzene, 790 mg of the boronic acid obtained in Preparation 2, 80 mg of palladium tetrakis and 1 g of potassium phosphate in 100 ml of dioxane are mixed together. The reaction medium is taken to reflux for 5 hours, another 80 mg of palladium tetrakis is added and the reaction medium taken to reflux for 24 hours. The mixture is chromatographed directly on silica eluting with a cyclohexane/ethyl acetate mixture 99/1. In this way 689 mg of crude product is collected, which is recrystallized from an ether-pentane mixture. The expected product is obtained with a yield of 60%.

Rf=0.6 cyclohexane/ethyl acetate 95/5
I.R. CHCl$_3$
Aromatics : 1601, 1590, 1500 cm$^{-1}$ Stage B: Formylation
4'-phenylmethoxy-2,3,5,6-tetrachloro-(1,1'-biphenyl)-4-carboxaldehyde 350 mg of the product prepared in the previous stage in 5 ml of tetrahydrofuran is cooled down to −78° C., 0.69 ml of a 1.45M solution of n-butyllithium in hexane is added dropwise then after agitation for 2 hours at −78° C. 90 µl of dimethylformamide in 0.4 ml of tetrahydrofuran is added dropwise. Agitation is carried out for 16 hours at −65° C., the reaction medium is poured into 13.6 g of ice and 2.7 ml of concentrated hydrochloric acid and the aqueous phase is extracted with ethyl acetate. After drying and concentration 320 mg of a mixture is obtained composed of the expected product and the starting product which is used directly in the following stage.

Rf=0.47 cyclohexane/ethyl acetate 95/5
NMR (CDCl$_3$) 200 MHz

| 10.35 (s) | C$\underline{H}$O |
| 7 (m) | Ph—O aromatic H's |
| 7.4 (m) | benzyl aromatic H's |
| 5.05 (s) | Ph—C$\underline{H}_2$—O |

Stage C: Reduction
4'-phenylmethoxy-2,3,5,6-tetrachloro-(1,1'-biphenyl)-4-methanol 320 mg of the product prepared in the previous stage is mixed with 16 ml of methanol, 34 mg of sodium borohydride and 0.5 ml of dichloromethane and the reaction medium is agitated for 15 minutes at ambient temperature. The reaction mixture is then poured into a saturated solution of ammonium chloride, the aqueous phase is extracted with ethyl acetate, dried and evaporated under reduced pressure. The residue is chromatographed on silica eluting with an ethyl acetate/cyclohexane mixture 10/90. In this way 130 mg of expected product is obtained.

Rf=0.56 cyclohexane/ethyl acetate 95/5.

Stage D: Deprotection
4'-hydroxy-2.3,5,6-tetrachloro-(1,1'-biphenyl)-4-methanol 130 mg of the product obtained in the previous stage in 5.5 ml of ethyl acetate is mixed at ambient temperature with 34 mg of palladium on carbon at 9.5%. The reaction medium is placed under a hydrogen atmosphere and agitation is carried out for 6 hours at 20° C. After filtration, the filtrate is evaporated under reduced pressure then purified by chromatography on silica eluting with a cyclohexane/ethyl acetate mixture 9/1. In this way 116 mg of crude product is collected which is recrystallized from dichloromethane. 47 mg of expected product is obtained.

Rf=0.14 cyclohexane/ethyl acetate 8/2
NMR (CD$_3$COCD$_3$) 250 MHz

| | |
|---|---|
| 2.23 (m) | CH$_2$O_H_ |
| 4.97 wide | Ph—O_H_ |
| 5.13 (s) | C_H_$_2$OH |
| 7.10, 6.96 (dd) | Ph—OH aromatic H's |

EXAMPLE 27

2,6-difluoro-4'-hydroxy-(1,1'-biphenyl)-4-methanol
Stage A: Protection
1,3-difluoro 5-[(tetrahydropyrannyloxy)methyl]-benzene 1.286 g of 3,5-difluorophenyl methanol is mixed under an inert atmosphere with 1.3 ml of 3,4-dihydropyranne, 155 mg of paratoluenesulphonic acid and 20 ml of dioxane and agitation is carried out at 20° C. for 2 hours 30 minutes. The reaction mixture is poured into a saturated solution of sodium bicarbonate, the dioxane is evaporated off under reduced pressure and the aqueous phase is extracted with ethyl acetate. The organic phase is dried then evaporated under reduced pressure. 1.81 g of expected product is collected.

Rf=0.42 cyclohexane/ethyl acetate 9/1
I.R. CHCl$_3$
Absence OH
Aromatics 1632, 1602 cm$^{-1}$ Stage B: Chlorination, Coupling and Deprotection of the Alcohol
2,6-difluoro-4'-phenylmethoxy-(1,1'-biphenyl)-4-methanol A solution of 1.04 g of the product obtained in the previous stage in 20 ml of tetrahydrofuran is cooled down to −78° C. and 3.7 ml of a solution of n-Butyllithium (1.5M in hexane) is added dropwise under an inert atmosphere then, after agitation for 15 minutes at −78° C., 5.5 ml of a solution of zinc chloride (1.0M in tetrahydrofuran) is added. After agitation for 30 minutes at −78° C., the temperature is allowed to return to 20° C. and 1.44 g of the product obtained in Stage A of Preparation 2 and 265 mg of Tetrakis (triphenyl phosphine)-palladium (0) is added. The reaction mixture is taken to reflux for 5 hours, poured into a saturated solution of ammonium chloride and the aqueous phase is extracted with dichloromethane. The organic phase is dried and concentrated under reduced pressure. The crude product in the form of an oil is used as it is in the following stage of deprotection of the alcohol.

The crude oil is dissolved in 30 ml of methanol and 2.3 ml of 2N hydrochloric acid is added. The reaction medium is agitated for 4 hours at 20° C. and poured into a saturated solution of sodium bicarbonate. After concentration of the methanol under reduced pressure, the aqueous phase is extracted with dichloromethane, the organic phase is dried and concentrated under reduced pressure. In this way 1.851 g of expected product is obtained.

Rf=0.32 cyclohexane/ethyl acetate 7/3
I.R. Nujol
Complex Absorption OH/NH Region
Aromatics 1640, 1612, 1582.1569, 1528, 1492 cm$^{-1}$ Stage C: Debenzylation
2,6-difluoro-4'-hydroxy-(1,1'-biphenyl)-4-methanol 32 mg of the product obtained in the previous stage in 5 ml of ethyl acetate is mixed at ambient temperature with 31 mg of palladium on carbon at 9.5%. The reaction medium is placed under hydrogen atmosphere and agitation is carried out for 28 hours at 20° C. After filtration, the filtrate is evaporated under reduced pressure. In this way 116 mg of crude product is collected which is recrystallized from dichloromethane. 18 mg of expected product is obtained.

Rf=0.18 cyclohexane/ethyl acetate 7/3
I.R. Nujol
Complex Absorption OH/NH Region
Aromatics 1636, 1615, 1598.1573, 1530 cm$^{-1}$

EXAMPLE 28

4'-hydroxy-2-trifluoromethyl-(1,1'-biphenyl)-4-methanol

Stage A: Coupling
4'-benzyloxy-2-trifluoromethyl-(1,1'-biphenyl)-4-carboxaldehyde By operating as in Example 22 Stage A, starting with 0.911 g of (3-trifluoromethyl-4-bromo-benzaldehyde) and after purification by chromatography on a silica column eluting with a cyclohexane/ethyl acetate mixture 95/5, 1.093 g of expected product is obtained.

Rf=0.33 cyclohexane/ethyl acetate (8/2)
I.R. (CHCl$_3$)
CHO 2736, 1706 cm$^{-1}$
Ar 1611 (F), 1580, 1565 (sh.) and 1520 cm$^{-1}$ Stage B: Deprotection and Reduction
4'-hydroxy-2-trifluoromethyl-(1,1'-biphenyl)-4-methanol 308 mg of the product obtained in the previous stage in 15 ml of ethyl acetate is mixed at ambient temperature with 290 mg of palladium on carbon at 9.5%. The reaction medium is placed under a hydrogen atmosphere and agitation is carried out for 12 hours at 20° C. After filtration, the filtrate is evaporated under reduced pressure. 215.7 mg of a mixture of debenzylated product and its reduced analogue is obtained which is used directly in the following reaction.

215.7 mg of the mixture prepared in the previous stage is mixed with 3 ml of methanol, 48 mg of sodium borohydride at 95% and agitation is carried out for 3 hours at ambient temperature. After concentration under reduced pressure, the reaction mixture is taken up in dichloromethane and washed with a saturated solution of ammonium chloride, dried and evaporated under reduced pressure. The crude reaction product is chromatographed on silica eluting with an ethyl acetate/cyclohexane mixture 2/8. In this way 99 g of expected product is obtained.

Rf=0.20 cyclohexane/ethyl acetate 7/3)
I.R. (Nujol)
Absence of C═O
General Absorption OH/NH Region
1615, 1600, 1520 (sh.) and 1492 cm$^{-1}$ Ar

EXAMPLE 29

4'-methyl-2'-trifluoromethyl-(1,1'-biphenyl)-4-ol

The operation is carried out as in Example 3 starting with 1.004 g of the biphenyl obtained in Stage A of the previous example and 216 mg of expected product is obtained as well as 373 mg of the product of Example 28 (R$_5$=CH$_2$OH)

Rf=0.49 cyclohexane/ethyl acetate 7/3
NMR CDCl$_3$/250 MHz

| | |
|---|---|
| 2.44 (s) | C_H_$_3$ |
| 7.19 (masked) | H'$_6$ |

| | |
|---|---|
| 7.34 (dm) | H'$_5$ |
| 7.53 (m) | H'$_3$ |
| 6.85 and 7.20 AA' BB' | Ph—O— |
| 4.74 (s) | mobile 1 H |

EXAMPLE 30

2,6-dinitro-4'-hydroxy-(1,1'-biphenyl)-4-methanol

Stage A: Esterification

Methyl 4-chloro-3,5-dinitro-benzoate 2.96 ml of SOCl$_2$ is added at 0° C., under an inert atmosphere and dropwise to 10 g of 3,5-dinitro-4-chlorobenzoic acid (JANSSEN) in 150 ml of methanol and agitation is carried out under reflux of methanol for 2 hours then for 15 hours at ambient temperature. The reaction medium is poured into ice and precipitation of the product is observed. After drying, 10.3 g of expected product is obtained.

Rf=0.45 cyclohexane/ethyl acetate 7/3

I.R. CHCl$_3$

| | |
|---|---|
| C═O | 1738 cm$^{-1}$ |
| Aromatics + NO2 | 1614, 1552 cm$^{-1}$ |

Stage B: Coupling

Methyl 2,6-dinitro-4'-phenylmethoxy-(1,1'-biphenyl)-4-carboxylate 10 g of the product of the previous stage in 100 ml of dimethylformamide is mixed under an inert atmosphere with 8.4 g of the product of Preparation 6 and 15.12 g of copper then agitation is carried out while bringing the temperature from 20 to 120° C. over 2 hours and maintaining for 30 minutes at 120° C. After filtration of the crude reaction product, the reaction medium is poured into a mixture of ice plus water and extracted with dichloromethane. The organic phase is dried, concentrated under reduced pressure and chromatographed on silica eluting with a cyclohexane/ethyl acetate mixture 8/2. In this way 9.1 g of expected product is obtained.

Rf=0.46 cyclohexane/ethyl acetate 7/3

NMR CDCl$_3$/200 MHz

| | |
|---|---|
| 4 (s) | COO<u>Me</u> |
| 7–7.15 | Ph—O |
| 7.35 | Ph—CH$_2$—O |
| 8.5 | 2 H ortho of COOMe |
| 5 | Ph—C<u>H</u>$_2$—O |

Stage C: Deprotection

Methyl 2,6-dinitro 4'-hydroxy (1,1'-biphenyl) 4-carboxylate 11 ml of trifluoroacetic acid is added to 1.3 g of the product obtained in the previous stage and agitation is carried out under reflux of acetic acid for 1 hour 30 minutes. The reaction medium is poured onto a mixture of ice plus water and extracted with dichloromethane. The organic phase is dried, concentrated under reduced pressure and chromatographed on silica eluting with a cyclohexane/ethyl acetate mixture 7/3. In this 330 mg of expected product is collected.

Rf=0.42 cyclohexane/ethyl acetate (7/3)

NMR CDCl$_3$/200 MHz

| | |
|---|---|
| 3.98 (s) | COO<u>Me</u> |
| 6.8–7.1 | aromatic 4H's |
| 8.49 | 2 H ortho of COOMe |

Stage D: Reduction 2,6-dinitro-4'-hydroxy-(1,1'-biphenyl)-4-methanol

The process is carried out in an equivalent manner to Example 5 Stage B starting with 330 mg of the product prepared in the previous stage. After purification by chromatography on silica eluting with a cyclohexane/ethyl acetate mixture 7/3, 71.8 mg of expected product is obtained., Rf=0.45 cyclohexane/ethyl acetate 7/3

M.p.=156–158° C.

NMR DMSO/250 MHz

| | |
|---|---|
| 4.69 (d) | Ph—C<u>H</u>$_2$OH |
| 5.73 (t) | Ph—CH$_2$O<u>H</u> |
| 6.81 and 7.05 AA' BB' | Ph—O— |
| 8.15 (s) | H$_3$, H$_5$ |
| 9.82 (s) mobile 1 H | |

EXAMPLE 31

2-amino-4'-hydroxy-6-nitro-(1,1'-biphenyl)-4-methanol 300 mg of the product prepared in Example 30 in 6 ml of tetrahydrofuran is mixed under an inert atmosphere with 0.64 ml of cyclohexene and 30 mg of Pd(OH)2 and agitation is carried out for 3 hours at ambient temperature then for 16 hours under reflux of tetrahydrofuran. After filtration the tetrahydrofuran is evaporated off, the reaction medium is taken up in ethyl acetate and the organic phase is extracted with 2N hydrochloric acid. The acid phase is adjusted to basic pH with 2N soda, then is extracted with ethyl acetate. The organic phase is dried and concentrated under reduced pressure. The crude product thus obtained is recrystallized from chloroform. In this way 26 mg of expected product is obtained.

Rf=0.11 dichloromethane/methanol 95/05)

M.p.=158° C.

NMR DMSO/250 MHz

| | |
|---|---|
| 4.44 (ws) | Ph—C<u>H</u>$_2$OH |
| 5.02 (ws) | NH$_2$ |
| 5.30 (ws) | mobile H |
| 5.73 (t) | Ph—CH$_2$O<u>H</u> |
| 6.83 (d) and 6.98 (d) | |
| 6.91 (ws) and 6.93 (ws) | H$_3$, H$_5$ CH$_2$OH |
| 9.57 (s) | mobile 1 H |

EXAMPLE 32

2-bromo-4'-hydroxy-6-iodo-(1,1'-biphenyl)-4-methanol

Stage A: Iodation of Aminated Biphenyl

Methyl 2-bromo-4'-[[(1,1-dimethylethyl)dimethylsilyl]oxy]-6-iodo-(1,1'-biphenyl)-4-carboxylate 4 g of iodine is added to a solution of 2.69 g of the product prepared in Stage A of Example 19, in 50 ml of chloroform, then, dropwise, 1.05 ml of terbutylnitrite is added and the reaction medium left under agitation under reflux for 1 hour 30 minutes. After the excess iodine is neutralized with a solution of sodium thiosulphate, the reaction medium is extracted with chloroform, dried and evaporated under reduced pressure. The crude product is purified by chromatography on a column eluting with a cyclohexane/ethyl acetate mixture 99/1. 3.075 g of expected product is obtained.

Rf=0.70 cyclohexane/ethyl acetate 80/20

NMR CDCl$_3$ 250 MHz

| | |
|---|---|
| 0.25 s | Si(C$\underline{H}_3$)$_2$ |
| 1.01 s | Si—C(C$\underline{H}_3$)$_3$ |
| 3.94 s | CO$_2$C$\underline{H}_3$ |
| 6.96 AA' BB' | Ph—O |
| 8.29 d and 8.52 d | H$_3$, H$_5$ |

Stage B: Reduction
2-bromo-4'-[[(1,1-dimethylethyl)dimethylsilyl]oxy]-6-iodo-(1,1'-biphenyl)-4-methanol 2 equivalents of an extemporaneous solution of diisobutylaluminium/nbutyl lithium/toluene/n-hexane is added under an inert atmosphere at −70° C., to a solution of 160 mg of the ester prepared in the previous stage in 2 ml of toluene, agitation is carried out for 3 hours at −70° C. and 19.4 mg of sodium borohydride in 0.5 ml of methanol is added. After agitation for 45 minutes outside the ice bath, the reaction medium is poured into ice-cooled water then extracted with ethyl acetate. After drying, then evaporation under reduced pressure, the crude product obtained is purified by chromatography eluting with a cyclohexane/ethyl acetate mixture 98/2 then 95/5. 141 mg of expected product is obtained which is used as it is in the following stage.

Rf=0.48 cycohexane/ethyl acetate 7/3

Stage C: Deprotection of the Phenol
2-bromo-4'-hydroxy-6-iodo-(1,1'-biphenyl)-4-methanol The operation is carried out in the same manner as in Example 11 Stage B starting with 141 mg of the product obtained in the previous stage. 81 mg of expected product is obtained.

Rf=0.26 cyclohexane/ethyl acetate 7/3

NMR

| | |
|---|---|
| 4.49 d | C$\underline{H}_2$OH |
| 5.40 t | CH$_2$O$\underline{H}$ |
| 7.65 and 7.88 d | H$_3$, H$_5$ |
| 6.8 to 6.92 AA' BB' | Ph—OH |
| 9.58 | Ph—O$\underline{H}$ |

EXAMPLE 33

2-bromo-4'-hydroxy-6-[3-(dimethylamino)-1-propynyl]-(1,1'-biphenyl)-4-methanol

Stage A: Coupling of the Brominated Diaryl with Propargylamine

Methyl 2-bromo-6-(3-dimethylamino-1-propynyl)-4'-[[(1,1-dimethylethyl)dimethylsilyl]oxy]-(1,1'-biphenyl)-4-carboxylate 2 ml of diethylamine, 4 mg of copper iodide, 24 mg of tetrakispalladium and 0.07 ml of propargylamine are added to a solution under an inert atmosphere of 226.7 mg of the product obtained in Stage A of Example 32 in 4 ml of DMF, then the reaction medium is taken to reflux for 30 minutes followed by pouring into ice-cooled water, extraction with ethyl acetate, drying, evaporation under reduced pressure and purification by chromatography eluting with a cyclohexane/ethyl acetate mixture 60/40. 82.3 mg of expected product is obtained.

Rf=0.49 100 % ethyl acetate

NMR CDCl$_3$ 250 MHz

| | |
|---|---|
| 0.23 s | Si(C$\underline{H}_3$)$_2$ |
| 1.00 s | Si—C(C$\underline{H}_3$)$_3$ |
| 2.08 s | N(C$\underline{H}_3$)$_2$ |
| 3.29 s | ≡C—C$\underline{H}_2$—N |
| 3.95 s | CO$_2$C$\underline{H}_3$ |
| 6.90 and 7.17 AA' BB' | Ph—O |
| 8.12 d and 8.24 d | H$_3$, H$_5$ |

Stage B: Reduction and Deprotection
2-bromo-4'-hydroxy-6-[3-(dimethylamino)-1-propynyl]-(1,1'-biphenyl)-4-methanol The operation is carried out in an equivalent manner to Example 32 Stages B and C, starting with 367 mg of the product obtained in the previous stage. 35 mg of expected product A is obtained as well as 44 mg of product B (R$_5$=CH(OH)nBu, Rf=0.36 dichloromethane/methanol: 9/1).

Product A:

Rf=0.25 dichloromethane/methanol 9/1

NMR DMSO 250 MHz

| | |
|---|---|
| 1.98 s | N(C$\underline{H}_3$)$_2$ |
| 3.29 s | ≡C—C$\underline{H}_2$—N |
| 4.50 d | C$\underline{H}_2$OH |
| 5.38 t, mobile | CH$_2$O$\underline{H}$ |
| 6.80 and 7.05 AA' BB' | Ph—O |
| 7.44 d and 7.62 d | H$_3$, H$_5$ |
| 9.51 mobile H | Ph—O$\underline{H}$ |

Product B: 2-bromo-alpha-butyl-4'-hydroxy-6-[3-(dimethylamino)-1-propynyl]-(1,1'biphenyl)-methanol NMR CDCl$_3$ 250 MHz

| | |
|---|---|
| 0.92 t | CH$_2$—CH$_2$—CH$_2$—C$\underline{H}_3$ |
| 1.36 m (4 H) | CH$_2$—C$\underline{H}_2$—C$\underline{H}_2$—CH$_3$ |
| 1.76 m | C$\underline{H}_2$—CH$_2$—CH$_2$—CH$_3$ |
| 2.09 s | N(C$\underline{H}_3$)$_2$ |
| 3.30 s | ≡C—C$\underline{H}_2$—N |
| 4.63 dd | C$\underline{H}$(nBu)OH |
| 5.38 t, mobile | CH$_2$O$\underline{H}$ |
| 6.82 and 7.14 AA' BB' | Ph—OH |
| 7.44 d and 7.61 d | H$_3$, H$_5$ |

EXAMPLE 34

2-(3-dimethylamino-1-propynyl)-4'-hydroxy-6-nitro-(1,1'-biphenyl)-4-methanol

The operation is carried out in an equivalent manner to Example 33 Stages A and B starting with 474.5 mg of the product prepared in Example 18 Stage C. 33 mg of the expected product is obtained recrystallized from ethyl ether.

Rf=0.14 CH$_2$Cl$_2$/MeOH 90/10

NMR (DMSO, 250 MHz)

| | |
|---|---|
| 1.99 s | N(C$\underline{H}_3$)$_2$ |
| 3.29 s | ≡C—C$\underline{H}_2$—N |
| 4.59 d | C$\underline{H}_2$OH |
| 5.52 t | CH$_2$O$\underline{H}$ |
| 6.79 and 7.08 d AA' BB4 | Ph—O |
| 7.71 and 7.71 d | H$_3$, H$_5$ |
| 9.12 ws mobile H | Ph—O$\underline{H}$ |

EXAMPLE 35:

4,4"-dihydroxy-(1,1':2', 1"-terphenyl)-5'-methanol
Stage A: Demethylation
Methyl 4,4"-dihydroxy-(1.1':2',1"-terphenyl)-5'-carboxylate 2.7 g of methyl 4,4"-dimethoxy-(1,1':2',1"-terphenyl)-5'-carboxylate (product prepared according to J. Med. Chem. (1989) 32 1814–1820) in 30 ml of dichloromethane is cooled down to −30° C., under an inert atmosphere, 2.7 ml of tribromoborane is added and agitation is carried out at −30° C. for 16 hours. The reaction medium is diluted with a saturated solution of sodium acetate, the aqueous phase is extracted with ethyl acetate, the organic phase is dried then evaporated. The crude reaction product is chromatographed on silica eluting with a cyclohexane/ethyl acetate mixture 70/30. In this way 814 mg of expected product is obtained.

Rf=0.31 cyclohexane/ethyl acetate 1/1
Stage B: Acetylation and Reduction
4,4"-dihydroxy-(1,1':2',1"-terphenyl)-5'-methanol 260 mg of the product obtained in the previous stage, in 8 ml of pyridine is cooled down under an inert atmosphere to 0° C., 0.08 ml of acetic anhydride is added and agitation is carried out for 20 minutes at 0° C. then the pyridine is evaporated off under reduced pressure. The 340 mg of crude reaction product obtained is used directly in the reduction reaction.

340 mg of the crude product in 6 ml of tetrahydrofuran is cooled down under an inert atmosphere to 0° C., 96 mg of LiAlH$_4$ is added and agitation is carried out for 30 minutes at 0° C. The medium is diluted in an ethyl acetate/water mixture and the aqueous phase is extracted with ethyl acetate. The organic phase is dried, evaporated under reduced pressure, and the residue is chromatographed on silica eluting with a cyclohexane/ethyl acetate mixture 80/20. In this way 66 mg of expected product is obtained.

Rf=0.31 cyclohexane/ethyl acetate 1/1
M.p.=214° C.
I.R. Nujol
absence of C=O
Possible absorption OH/NH
Aromatics 1610, 1590, 1516 cm$^{-1}$

EXAMPLE 36

2,6-dichloro-4'-hydroxy-5'-(phenylmethyl)-(1,1'-biphenyl)-4-methanol
Stage A: Deprotection+Rearrangement
2,6-dichloro-4'-hydroxy-5'-(phenylmethyl)-(1,1'-biphenyl)-4-carboxaldehyde The mixture constituted by 522 mg of the benzylated diphenyl obtained in Example 24 Stage D and 10 ml of trifluoroacetic acid is heated under reflux for 1 hour 30 minutes. The reaction medium is poured into 100 ml of water, then extracted with ethyl acetate, dried and evaporated under reduced pressure. The crude product is purified by reversed-phase chromatography eluting with a methanol/water mixture 60/40 then 80/20. 152 mg of expected product is obtained as well as 147 mg of the debenzylated analogue.

Rf=0.21 cyclohexane/ethyl acetate 80/20
NMR CDCl$_3$, 200 MHz

| | |
|---|---|
| 4.05 s | C$\underline{H}_2$Ph |
| 7.05 m 2 H | H$_2$', H$_6$' |
| 6.95 d 1 H | H$_3$' |
| 7.5 7.2 m 5 H | benzyl |
| 7.8 s 2 H | H$_3$, H$_5$ |
| 9.95 s 1 H | C$\underline{H}$O |

Stage B: Reduction
2,6-diphenyl-4'-hydroxy-5'-(phenylmethyl)-(1,1'-biphenyl)-4-methanol The operation is carried out in an equivalent manner to Example 2 starting with 140.4 mg of the aldehyde of the previous stage and 58 mg of expected product is obtained.

Rf=0.27 cyclohexane/ethyl acetate 7/3
NMR CDCl$_3$, 200 MHz

| | |
|---|---|
| 4.03 s 2 H | C$\underline{H}_2$Ph |
| 7.03 m 2 H | H$_2$', H$_6$' |
| 6.86 d 1 H | H$_3$' |
| 7.16 7.34 m 5 H | benzyl |
| 7.39 s 2 H | H$_3$, H$_5$ |
| 4.68 ws 2 H | C$\underline{H}_2$OH |
| 1.86 ws 1 H | Ph—O$\underline{H}$ |
| 4.89 ws 1 H | CH$_2$O$\underline{H}$ |

By operating in a similar manner to the above examples, starting with the appropriate compounds, the following compounds were prepared:

EXAMPLE 37

2-bromo 6-[[4-[2-(dimethylamino) ethoxy] phenyl] hydroxymethyl] 4'-hydroxy (1,1'-biphenyl) 4-methanol
Rf=0.19 (CH$_2$Cl$_2$/MeOH 8/2)

EXAMPLE 38

[6-bromo 4'-hydroxy 4-(hydroxymethyl) (1,1'-biphenyl) 2-yl] [4-[2-(dimethylamino) ethoxy] phenyl] methanone.
Rf=0.16 (CH$_2$Cl$_2$/MeOH 9/1)

EXAMPLE 39

6'-bromo 4-[2-(dimethylamino) ethoxy] 4"-hydroxy (1,1':2',1"-terphenyl) 4'-methanol
Rf=0.13 (CH$_2$Cl$_2$/MeOH 9/1)

EXAMPLE 40

4-[2-(dimethylamino) ethoxy] 4"-hydroxy 6'-nitro (1,1':2', 1"-terphenyl) 4'-methanol
Rf=0.11 (CH$_2$Cl$_2$/MeOH 9/1)

EXAMPLE 41

6'-chloro 4,4"-dihydroxy (1.1':2',1"-terphenyl) 4'-methanol
Rf=0.36 (CH$_2$Cl$_2$/MeOH 9/1).

Pharmaceutical Composition
Tablets were prepared corresponding to the following general formula:

| | |
|---|---|
| product of Example 7 | 50 mg |
| Excipient (talc, starch, magnesium stearate) | 120 mg |
| qs for a tablet completed at | |

Pharmacological Study of the Products of the Invention

Oestrogen Receptor of a Rat's Uterus (ROR):

Female rats of 280–300 g and castrated 24 hours beforehand, are sacrificed, the uteri are removed, then homogenized at 0° C., using a teflon-glass Potter in a buffered solution BS (10 mM Tris, 0.25 M saccharose, HCl pH 7.4) (1 g of tissue per 10 ml of BS). The homogenate is then ultracentrifuged (209,000 g×30mn.) at 0° C. The supernatant aliquots thus obtained are incubated at 0° C. for 24 hours, with a constant concentration (2.5 $10^{-9}$M) of tritiated oestrodiol in the presence of increasing concentrations either of unlabelled oestradiol (0–1000×$10^{-9}$M), or of unlabelled product to be tested (25000×$10^{-9}$M). The concentration of bound tritiated oestradiol (B) is then measured in each incubate by the carbon-dextran adsorption technique.

Human Oestrogen Receptor (HOR)

A cytosolic extract of SF9 cells containing the recombinant human oestrogen receptor is obtained by overexpression in an insect-Baculovirus cell system, according to the general methodology described by N. R. WEBB et al. (Journal of Methods in Cell and Molecular Biology, (1990) Vol.2 No. 4, 173–188) and the application of which is described for the expression of human hormonal receptors, for example the human glucocorticoid receptor (G. SRINIVASAN et al. Molecular Endocrinology (1990) vol 4 No. 2 209–216).

The BaculoGold Transfection Kit (PharMingen, reference 21000K) is used to generate the recombinant baculovirus containing the cDNA fragment described in the expression vector HEGO by L. TORA et al. (The EMBO Journal (1989) vol. 8 No. 7 1981–1986), containing the coding region for the wild-type human oestrogen receptor with a glycine in position 400.

The recombinant virus thus obtained is used to express the oestrogen receptor in the SF9 insect cells (ATCC CRL1711), according to the known methodology mentioned previously.

$2*10^7$ SF9 cells are cultured in a 175 cm$^2$ "Falcon" flask in the TNM-FH "SIGMA" medium supplemented by 10% of foetal calf serum (FCS) and by 50 microgram/ml of gentamycin. After infection then incubation at 27° C. for 40 to 42 hours, the cells are lysed in 1 ml of lysis buffer (Tris 20 mM-HCl pH8, EDTA 0.5 mM, DTT 2 mM, Glycerol 20%, KCl 400 mM) with a freezing-thawing cycle which is repeated another two times. The supernatant, containing the recombinant human oestrogen receptor is kept in liquid nitrogen by 0.5 ml doses.

The supernatant is incubated at 0° C. for 24 hours (long t) or 3 hours (short t) with a constant concentration (T) of tritiated oestradiol in the presence of increasing concentrations of either unlabelled oestradiol (0–1000×$10^{-9}$M), or of unlabelled product to be tested (0–25000×$10^{-9}$M). The concentration of bound tritiated oestradiol (B) is then measured in each incubate by the technique of adsorption with carbon dextran.

Calculation of the Relative Bond Affinity (RBA):

The following two curves are drawn: the percentage of bound tritiated hormone 100×B/B0 as a function of the logarithm of the concentration of unlabelled reference hormone or as a function of the concentration of unlabelled test product.

The straight line of the equation $$I_{50}=B0/B0+B\min/B0)/2=100\ (1+B\min/B0)=50\ (1+B\min/B0)$$

is determined.

B0=concentration of bound tritiated hormone in the absence of any unlabelled product.

B=concentration of bound tritiated hormone in the presence of a concentration X of unlabelled product.

B min=concentration of bound tritiated hormone for an incubation of this tritiated hormone at a concentration (T) in the presence of a large excess of unlabelled reference hormone (1000×$10^{-9}$M) for the human receptor.

The intersections of the straight line $I_{50}$ and the curves allow the evaluation of the concentrations of unlabelled reference hormone (CH) and of the unlabelled test product (CX) which inhibit by 50% the binding of the tritiated hormone on the receptor.

The relative bond affinity (RBA) of the test product is calculated by the equation: RBA=100(CH)/(CX).

The results obtained are as follows:

| | | HOR oestradiol = 100 | |
|---|---|---|---|
| Examples | ROR | short t | long t |
| (Ex 2) | 12.5 | 425 | 74 |
| (Ex 24) | 3 | 104 | 35 |
| (Ex 30) | 2 | 24 | 5 |
| (Ex 26) | — | — | 5.5 |
| (Ex 1) | — | — | 5.5 |
| (Ex 6) | — | — | 4.5 |
| (Ex 25) | — | 12 | 5 |
| (Ex 13) | 0.8 | 24 | 7.5 |
| (Ex 28) | 2 | 33 | 8 |
| (Ex 29) | 0.15 | — | 0.6 |
| (Ex 4) | 4 | — | 22 |
| (Ex 18) | 5 | — | 34 |
| (Ex 36) | 8 | — | 0.07 |
| (Ex 7) | 9.5 | — | 50 |

Conclusion

Certain of the products have an affinity which can range up to 425% of the oestradiol which is a new fact for this family of molecules.

What is claimed is:

1. A method of treating osteoporosis in warm-blooded animals comprising administering to warm-blooded animals in need thereof an effective amount to treat osteoporosis of a compound selected from the group consisting of a compound of the formula:

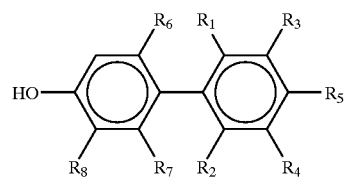

wherein $R_1$ and $R_2$ are individually selected from the group consisting of a) hydrogen, halogen, —OH, —CF$_3$, NO$_2$, —NH$_2$, alkoxy of 1 to 8 carbon atoms, alkylthio of 1 to 8 carbon atoms,

wherein $R_A$ and $R_B$ are individually alkyl of 1 to 8 carbon atoms or together with the nitrogen to which they are attached form a saturated or unsaturated heterocycle of 5 to 6 ring members optionally containing a heteroatom selected from the group consisting of oxygen, sulfur and nitrogen, b) optionally substituted alkyl, alkenyl and alkynyl of up to 8 carbon atoms, c) optionally substituted aryl of 6 to 14 carbon atoms, optionally substituted aralkyl of 7 to 15 carbon atoms, —CH(OH)—Y and

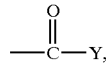

Y is selected from the group consisting of i) optionally substituted alkyl, alkenyl and alkynyl of up to 8 carbon atoms and ii) optionally substituted aryl of 6 to 14 carbon atoms or $R_1$ and $R_3$ form —CH=CH—CH=CH—, $R_3$ and $R_4$ are individually selected from the group consisting of hydrogen, halogen and alkyl of 1 to 8 carbon atoms, $R_6$ and $R_7$ are individually hydrogen or halogen, $R_8$ is hydrogen or optionally substituted benzyl and $R_5$ is selected from the group consisting of —[A]—CHO, —[A]—CH$_3$, —[A]—C(OH)ZZ' and

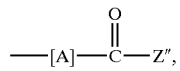

—[A]—is selected from the group consisting of a single bond and alkylene, alkenylene and alkynylene of up to 8 carbon atoms and Z, Z' and Z" are individually selected from the group consisting of a) hydrogen and alkyl, alkenyl and alkynyl of up to 8 carbon atoms and b) optionally substituted aryl of 6 to 14 carbon atoms and its non-toxic, pharmaceutically acceptable addition salts with acids and bases with the proviso that compounds wherein $R_5$ is

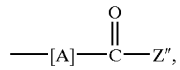

and A is a single bond, Z" is alkyl of 1 to 8 carbon atoms and $R_1$ to $R_8$ are all hydrogen are excluded.

2. The method of claim 1 wherein the compound is selected from the group consisting of:
2,6-dibromo-4'-hydroxy-(1,1'-biphenyl)-4-methanol,
2,6-dichloro-4'-hydroxy-(1,1'-biphenyl)-4-methanol,
2,6-dinitro-4'-hydroxy-(1,1'-biphenyl)-4-methanol,
4,4"-dihydroxy-(1,1':2',1"-terphenyl)-5'-methanol,
1-[2-chloro-4'-hydroxy-3-methyl-6-isopropyl-(1,1'-biphenyl-4-yl)]-ethanone,
2-bromo-4'-hydroxy-6-nitro-(1,1'-biphenyl)-4-methanol,
1-[2-chloro-4'-hydroxy 3-methyl-6-isopropyl-(1,1'-biphenyl-4-yl)]-ethanol,
4'-hydroxy-2-trifluoromethyl-(1,1'-biphenyl)-4-methanol,
4'-methyl-2'-trifluoromethyl-(1,1'-biphenyl)-ol,
2,6-dichloro-4'-hydroxy-(1,1'-biphenyl)-4-carboxaldehyde,
2-chloro-4'-hydroxy-6-isopropyl-(1,1'-biphenyl)-4-methanol,
2-chloro-4'-hydroxy-6-trifluoromethyl-(1,1'-biphenyl)-4-methanol,
2,6-dichloro-4'-hydroxy-5'-benzyl-(1,1'-biphenyl)-4-methanol,
2-bromo 6-[[4-[2-dimethylamino) ethoxy] phenyl] hydroxyethyl] 4'-hydroxy (1,1'-biphenyl) 4-methanol,
[6-bromo 4'-hydroxy 4-(hydroxymethyl) (1,1'-biphenyl) 2-yl) [4-[2-dimethylamino) ethoxy] phenyl] methanone,
6'-bromo 4-(2-(dimethylamino) ethoxy] 4"-hydroxy (1,1':2',1"-terphenyl) 4'-methanol,
4-[2-(dimethylamino) ethoxy] 4"-hydroxy 6'-nitro (1,1':2',1"-terphenyl) 4'-methanol and
6'-chloro 4,4"-dihydroxy (1,1':2',1"-terphenyl) 4'-methanol.

3. The method of claim 1 wherein the active compound has the formula:

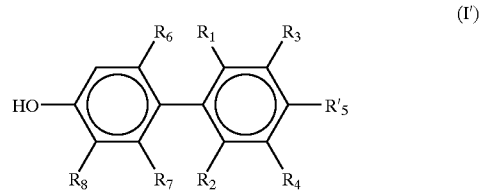

in which
either $R'_5$ is —[A]—CHO as defined in claim 17 and $R_1$, $R_2$, $R_3$, $R_4$, $R_6$, $R_7$ and $R_8$ are as defined as in claim 17, it being understood that when [A] is a single bond and $R_3$, $R_4$, $R_6$, $R_7$ and $R_8$ are hydrogens, $R_1$ and $R_2$ cannot simultaneously represent hydrogen,
or $R'_5$ is —C(OH)ZZ' as defined in claim 17 and $R_1$, $R_2$, $R_3$, $R_4$, $R_6$, $R_7$, and $R_8$ are as defined in claim 17, it being understood that when $R_3$, $R_4$, $R_6$, $R_7$, and $R_8$ are hydrogens, $R_1$ and $R_2$ cannot simultaneously be hydrogen,
or $R'_5$ is —[A]—CH$_3$ as defined in claim 17 and $R_1$, $R_2$, $R_3$, $R_4$, $R_6$, $R_7$, and $R_8$, are as defined in claim 17, it being understood that when $R_3$, $R_4$, $R_6$, $R_7$ and $R_8$ are hydrogens, $R_1$, and $R_2$ cannot simultaneously each be hydrogen, and it being understood that $R_1$, $R_2$, $R_3$ or $R_4$ cannot be alkyl or halogen,
or $R'_5$ is [A]—C(O)Z" as defined in claim 17, $R_1$, $R_2$, $R_3$, $R_4$, $R_6$, $R_7$ and $R_8$ are as defined in claim 17, it being understood that when [A] is a single bond, $R_3$, $R_4$, $R_6$, $R_7$ and $R_8$ are hydrogen, and Z" is alkyl of 1 to 8 carbon atoms, so $R_1$ and $R_2$ cannot simultaneously each be hydrogen, or cannot be a nitro or hydroxyl, as well as the addition salts with pharmaceutically acceptable acids and bases.

4. The method of clam 1 wherein the active compound has the formula:

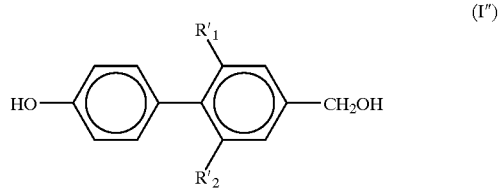

in which $R'_1$ is an aryl of 6 to 14 carbon atoms and optionally substituted, $R'_2$ is halogen, nitro or amino, as well as the addition salts with pharmaceutically acceptable acids and bases.

5. The method of claim 1 wherein —[A]— is a single bond.

6. The method of claim 1 wherein $R'_5$ is —CH$_2$OH.

7. The method of claim 1 wherein $R_6$, $R_7$ and $R_8$ are hydrogen.

8. The method of claim 1 wherein $R_1$ and $R_2$ are individually halogen and $R_3$, $R_4$, $R_5$, $R_6$, and $R_7$ and $R_8$ are hydrogen.

9. The method of claim 4 wherein $R'_1$ is phenyl substituted with dialkylaminoalkoxy of 3 to 16 carbon atoms.

* * * * *